United States Patent
Bäck et al.

(10) Patent No.: US 11,045,361 B2
(45) Date of Patent: Jun. 29, 2021

(54) ARRAY OF DISPOSABLE PANT-TYPE GENDER-SPECIFIC ABSORBENT ARTICLES

(71) Applicant: Essity Hygiene and Health Aktiebolag, Gothenburg (SE)

(72) Inventors: Lucas Bäck, Gothenburg (SE); Karin Ljungberg, Gothenburg (SE); Anna Stenberg, Gothenburg (SE)

(73) Assignee: Essity Hygiene and Health Aktiebolag, Gothenburg (SE)

(*) Notice: Subject to any disclaimer, the term of this patent is extended or adjusted under 35 U.S.C. 154(b) by 0 days.

(21) Appl. No.: 16/640,550

(22) PCT Filed: Aug. 24, 2017

(86) PCT No.: PCT/SE2017/050854
§ 371 (c)(1),
(2) Date: Feb. 20, 2020

(87) PCT Pub. No.: WO2019/039981
PCT Pub. Date: Feb. 28, 2019

(65) Prior Publication Data
US 2020/0297550 A1    Sep. 24, 2020

(51) Int. Cl.
*A61F 13/15* (2006.01)
*A61F 13/496* (2006.01)
(Continued)

(52) U.S. Cl.
CPC ...... *A61F 13/496* (2013.01); *A61F 13/49011* (2013.01); *A61F 13/55105* (2013.01); *A61F 2013/49088* (2013.01)

(58) Field of Classification Search
CPC .............. A61F 13/496; A61F 13/49011; A61F 13/55105; A61F 13/47; A61F 13/471;
(Continued)

(56) References Cited

U.S. PATENT DOCUMENTS

2010/0108554 A1* 5/2010 Melius ............... A61F 13/491
                                                                  206/438
2013/0138072 A1* 5/2013 Morimoto ......... A61F 13/49017
                                                                  604/385.29
(Continued)

FOREIGN PATENT DOCUMENTS

WO      03047488 A1    6/2003
WO    2007133127 A1   11/2007
(Continued)

OTHER PUBLICATIONS

International Search Report and Written Opinion for International Application No. PCT/SE2017/050854, dated Apr. 6, 2018, 11 pages.

*Primary Examiner* — Jacqueline F Stephens
(74) *Attorney, Agent, or Firm* — Buchanan Ingersoll & Rooney PC

(57) ABSTRACT

An array of disposable pant-type gender-specific absorbent articles adapted for female and male users. The array has a first subarray including first and second sizes for female users; and a second subarray including third and fourth sizes for male users. Each absorbent article in the array has a transversely elasticised waist portion. At least one of the first and second size absorbent articles has a first circumferential length of the waist portion in a relaxed state and a second circumferential length of the waist portion in an extended state. At least one of the third and fourth size absorbent articles has a third circumferential length of the waist portion in a relaxed state and a fourth circumferential length of the waist portion in an extended state. The first circumferential length is smaller than the third circumferential length, and the second circumferential length is equal to the fourth circumferential length.

27 Claims, 9 Drawing Sheets

(51) Int. Cl.
*A61F 13/49* (2006.01)
*A61F 13/551* (2006.01)

(58) Field of Classification Search
CPC ...... A61F 13/472; A61F 13/49; A61F 13/551; A61F 2013/49088
See application file for complete search history.

(56) References Cited

U.S. PATENT DOCUMENTS

| | | |
|---|---|---|
| 2013/0211355 A1 | 8/2013 | Nishikawa et al. |
| 2014/0378932 A1 | 12/2014 | Seitz et al. |
| 2015/0065982 A1 | 3/2015 | Hamilton et al. |
| 2015/0283004 A1 | 10/2015 | Seitz et al. |
| 2015/0320611 A1 | 11/2015 | Seitz et al. |
| 2015/0320612 A1 | 11/2015 | Seitz et al. |
| 2015/0320613 A1 | 11/2015 | Seitz et al. |
| 2015/0320614 A1 | 11/2015 | Seitz et al. |
| 2015/0320619 A1 | 11/2015 | Seitz et al. |
| 2016/0374871 A1 | 12/2016 | Seitz et al. |

FOREIGN PATENT DOCUMENTS

| | | |
|---|---|---|
| WO | 2013002691 A1 | 1/2013 |
| WO | 2014098683 A1 | 6/2014 |
| WO | 2018106160 A1 | 6/2018 |

\* cited by examiner

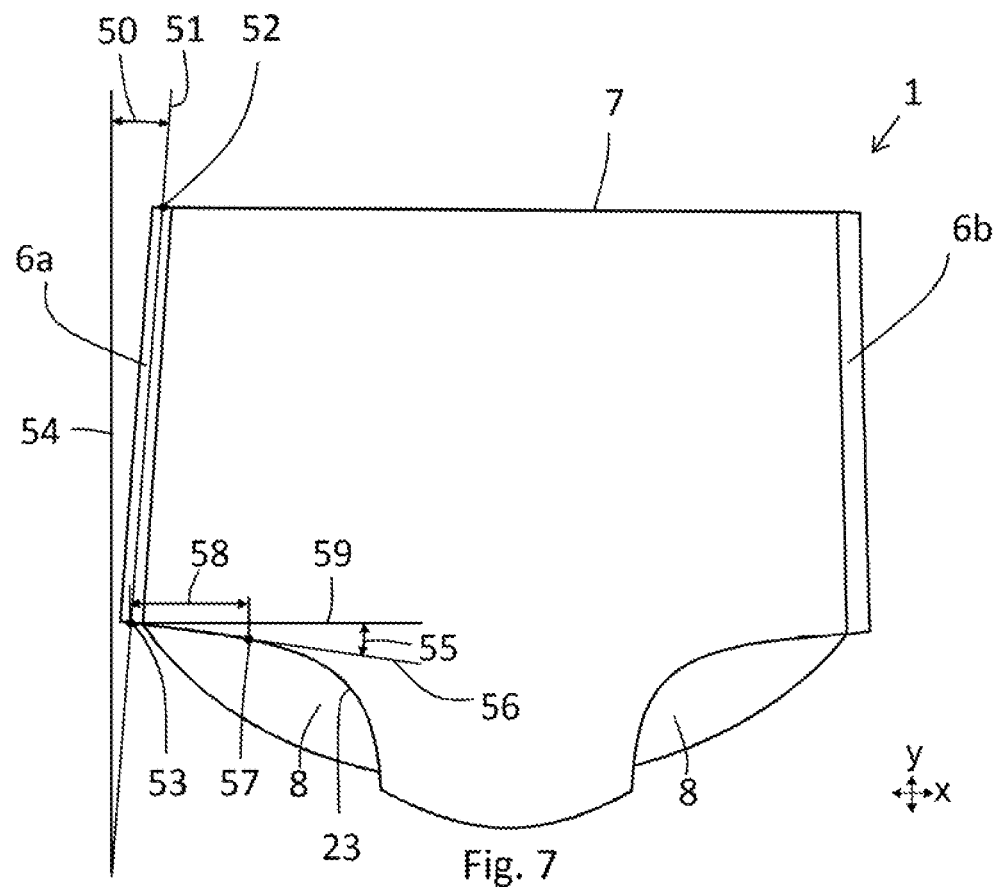
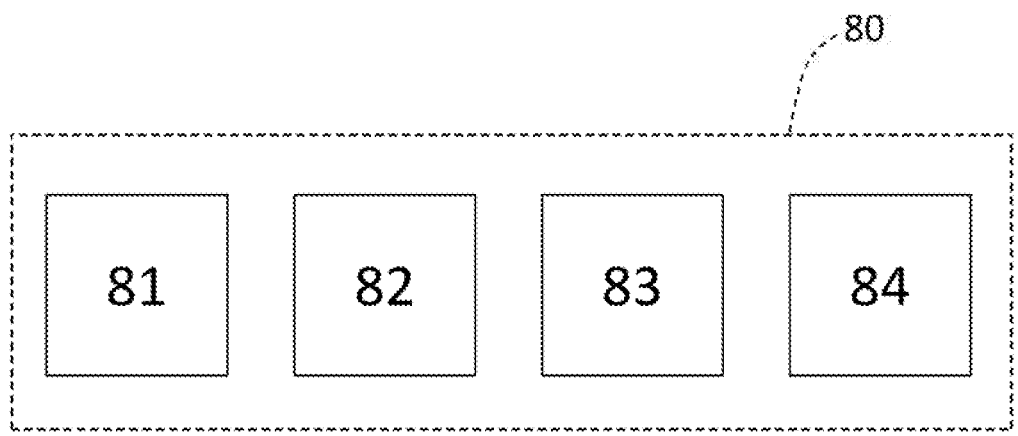
FIG.8

ARRAY OF DISPOSABLE PANT-TYPE GENDER-SPECIFIC ABSORBENT ARTICLES

CROSS REFERENCE TO RELATED APPLICATIONS

This is a U.S. National Phase application of PCT/SE2017/050854, filed Aug. 24, 2017, the disclosure of which is incorporated herein by reference in its entirety for all purposes.

TECHNICAL FIELD

The disclosure relates to an array of disposable pant-type gender-specific absorbent articles adapted for female and male users. The array comprises a first subarray of absorbent articles including a first size absorbent article adapted for female users and a second size absorbent article adapted for female users, and a second subarray of absorbent articles including a third size absorbent article for male users and a fourth size absorbent article adapted for male users. This disclosure also relates to an array of packages comprising an array of disposable pant-type gender-specific absorbent articles.

BACKGROUND

In the field of disposable pant-type absorbent articles there is a general desire to provide absorbent articles with increased comfort and fit as well as discrete underwear-like visual appearance. Due to anatomical differences between men and women it is not always suitable to have only one kind of absorbent articles. However, having different absorbent articles for males and females requires different manufacturing apparatuses leading to increased cost. Thus, further improvements in terms of comfort, fit and discrete underwear-like visual appearance while maintaining a low manufacturing cost is desirable.

SUMMARY

It is an object of the present disclosure to provide an array of disposable pant-type gender-specific absorbent articles adapted for female and male users addressing the above mentioned desires. This object is achieved at least partly by the features of the independent claims. Variations of the disclosure are found in the dependent claims.

The disclosure relates to an array of disposable pant-type gender-specific absorbent articles adapted for female and male users. The array comprises a first subarray of absorbent articles including a first size absorbent article adapted for female users and a second size absorbent article adapted for female users, and a second subarray of absorbent articles including a third size absorbent article for male users and a fourth size absorbent article adapted for male users. Each absorbent article of the array has a longitudinal direction and a transverse direction and comprises a front panel having a waist edge and a pair of side edges, a back panel having a waist edge and a pair of side edges, and an absorbent insert located mainly in a crotch portion of the absorbent article and being connected to the front and back panels and having an absorbent core. The front and back panels are joined to each other at opposite side edges by side seams forming a waist opening and two leg openings. Moreover, each absorbent article in the array comprises a transversely elasticised waist portion extending along the waist opening and a transversely elasticised body portion located adjacent to the waist portion, and at least one of said first and second size absorbent articles has a first circumferential length of the waist portion in a relaxed state and a second circumferential length of the waist portion in an extended state, and at least one of said third and fourth size absorbent articles has a third circumferential length of the waist portion in a relaxed state and a fourth circumferential length of the waist portion in an extended state. The circumferential length of the waist portion in the relaxed state is measured according to the method described in the specification with a tension of 3 Newton, and the circumferential length of the waist portion in the extended state is measured according to the method described in the specification with a tension of 80 Newton. The third circumferential length is more than 10%, specifically more than 15% larger than the first circumferential length, and the fourth circumferential length is less than 5%, specifically less than 3%, larger than the second circumferential length.

The claimed array of disposable pant-type gender-specific absorbent articles provides a solution to the above-mentioned problem by having at least one female absorbent article and one male absorbent article sharing essentially the same width dimension of the front and back panels 3, 4 in the extended state of the absorbent articles, such that the cost for an array of gender-specific absorbent articles is kept relatively low, while the shape and form of the male and female absorbent articles in the relaxed state of the absorbent articles is adapted to have a better fit for each specific gender. The shape and form of the male and female absorbent articles in a relaxed state of the absorbent articles is adapted by varying the degree of gathering of the sheet material of the front and/or back panel in the transverse direction X, such that circumferential length of the waist portion in the relaxed state is adapted to a typical hip shape of each gender. Moreover, the circumferential length of the waist portion in the relaxed state can be varied and adapted relatively cost-efficiently by for example adapting the waist and/or body elastic feature.

Consequently, an array of gender-specific absorbent articles is provided that comprises absorbent articles specifically adapted for each gender for enabling comfortable absorbent articles with discrete underwear-like visual appearance, while the amount of differences between male and female gender-specific absorbent articles are kept at a very low level for keeping the increased cost for manufacturing the array of gender-specific absorbent articles at a low level.

The disclosure also relates to an array of disposable pant-type gender-specific absorbent articles adapted for female and male users. The array comprises a first subarray of absorbent articles including a first size absorbent article adapted for female users and a second size absorbent article adapted for female users, and a second subarray of absorbent articles including a third size absorbent article for male users and a fourth size absorbent article adapted for male users. Each absorbent article of the array has a longitudinal direction Y and a transverse direction X and comprises a front panel having a waist edge and a pair of side edges, a back panel having a waist edge and a pair of side edges, and an absorbent insert located mainly in a crotch portion of the absorbent article and being connected to the front and back panels and having an absorbent core. The front and back panels are joined to each other at opposite side edges by side seams forming a waist opening and two leg openings. Each absorbent article in the array comprises a first acute angle α defined by a first line extending between an uppermost point of the side seam and a lowermost point of the side seam with the article in a relaxed state and a second line extending in the longitudinal direction Y, and wherein the first acute angle α of each of the first and second size absorbent articles is larger than the first acute angle α of each of the third and fourth size absorbent articles.

By providing the female absorbent articles of the array with a relatively narrow waist and wider hip they are adapted for providing increased comfort, fit and underwear-like appearance. Consequently, an array of gender-specific absorbent articles is provided that comprises absorbent articles specifically adapted for each gender for enabling comfortable absorbent articles with discrete underwear-like visual appearance, while the amount of differences between male and female gender-specific absorbent articles are kept at a very low level for keeping the increased cost for manufacturing the array of gender-specific absorbent articles at a low level.

The first size absorbent article may be smaller than the second size absorbent article. This may be accomplished by having the circumferential length of the waist portion in the extended state of the first size absorbent article smaller than the circumferential length of the waist portion in the extended state of the second size absorbent article.

The third size absorbent article may be smaller than the fourth size absorbent article. This may be accomplished by having the circumferential length of the waist portion in the extended state of the third size absorbent article smaller than the circumferential length of the waist portion in the extended state of the fourth size absorbent article.

The circumferential length of the waist portion in the extended state of the first size absorbent article may be substantially equal with the circumferential length of the waist portion in the extended state of the third size absorbent article. By having the male and female absorbent articles sharing as many features as possible the cost for providing a gender-specific array of absorbent articles is kept low.

The circumferential length of the waist portion in the extended state of the second size absorbent article may be substantially equal with the circumferential length of the waist portion in the extended state of the fourth size absorbent article. By having the male and female absorbent articles sharing as many features as possible the cost for providing a gender-specific array of absorbent articles is kept low.

The circumferential length of the waist portion in the relaxed state of the first size absorbent article may be smaller than the circumferential length of the waist portion in the relaxed state of the third size absorbent article. By having a relatively large amount of gathering of the waist portion of the female absorbent articles compared with the male absorbent articles a cost-efficient approach for adapting the absorbent articles to each specific gender is obtained.

The circumferential length of the waist portion in the relaxed state of the second size absorbent article may be smaller than the circumferential length of the waist portion in a relaxed state of the fourth size absorbent article. By having a relatively large amount of gathering of the waist portion of the female absorbent articles compared with the male absorbent articles a cost-efficient approach for adapting the absorbent articles to each specific gender is obtained.

The first size absorbent article may be smaller than the second size absorbent article. This may be accomplished by having a circumferential length of the body portion in an extended state of the first size absorbent article smaller than a circumferential length of the body portion in an extended state of the second size absorbent article, wherein the circumferential length of the body portion in the extended state is measured according to the method described in the specification with a tension of 80 Newton.

The third size absorbent article may be smaller than the fourth size absorbent article. This may be accomplished by having the circumferential length of the body portion in an extended state of the third size absorbent article smaller than the circumferential length of the body portion in an extended state of the fourth size absorbent article, wherein the circumferential length of the body portion in the extended state is measured according to the method described in the specification with a tension of 80 Newton.

The circumferential length of the body portion in an extended state of the first size absorbent article may be substantially equal with the circumferential length of the body portion in an extended state of the third size absorbent article, wherein the circumferential length of the body portion in the extended state is measured according to the method described in the specification with a tension of 80 Newton. By having the male and female absorbent articles sharing as many features as possible the cost for providing a gender-specific array of absorbent articles is kept low.

The circumferential length of the body portion in an extended state of the second size absorbent article may be substantially equal with the circumferential length of the body portion in an extended state of the fourth size absorbent article, wherein the circumferential length of the body portion in the extended state is measured according to the method described in the specification with a tension of 80 Newton. By having the male and female absorbent articles sharing as many features as possible the cost for providing a gender-specific array of absorbent articles is kept low.

Each absorbent article in the array may comprise a first acute angle defined by a first line extending between an uppermost point of the side seam and a lowermost point of the side seam with the article in a relaxed state and a second line extending in the longitudinal direction, wherein the first acute angle of each of the first and second size absorbent articles is larger than the first acute angle of each of the third and fourth size absorbent articles. By providing the female absorbent articles of the array with a relatively narrow waist and wider hip they are adapted for providing increased comfort, fit and underwear-like appearance.

Each absorbent article in the array comprises a second acute angle defined by a third line running through the lowermost point of the side seam and a point along the front leg edge at a distance of 5 cm from the lowermost point of the side seam in the transverse direction with the article in a relaxed state and fourth line running in the transverse direction, wherein the second acute angle of each of the first and second size absorbent articles is larger than the second acute angle of each of the third and fourth size absorbent articles. By providing the female absorbent articles of the array with a relatively narrow waist and wider hip they are adapted for providing increased comfort, fit and underwear-like appearance.

A smallest longitudinal distance L between a side edge of the front panel and an oppositely located side edge of the back panel of each absorbent article in the array may be essentially the same. This enables use of more common manufacturing equipment, such that the manufacturing cost for the array of gender-specific absorbent articles can be reduced.

The front panel in the array may comprise a first elastic region and a second elastic region, and each back panel in the array may comprise a third elastic region and a fourth elastic region, wherein the first and third elastic regions may define the transversely elasticised waist portion extending along the waist opening and the second and fourth elastic regions may define the transversely elasticised body portion.

The transversely elasticised waist portion and/or the transversely elasticised body portion may comprise an elastic web material, such as an elastic nonwoven or elastic film laminate. An elastic web material may for example comprise an elastic film material or elastic nonwoven sandwiched between two layers of nonwoven material.

The transversely elasticised waist portion of each absorbent article of the first subarray may comprise an elastic film laminate with additional elastic threads, and the transversely elasticised waist portion of each absorbent article of the second subarray may comprise an elastic film laminate that is free from any additional elastic threads. By having additional elastic threads in the elasticised waist portion of the female absorbent articles relatively high elastic tension may be provided in the elasticised waist portion of the female articles, and by having the transversely elasticised waist portion of the male absorbent article comprising an elastic film laminate that is free from any additional elastic threads relatively low elastic tension may be provided in the elasticised waist portion of the male articles. Thereby, the shape and form of the male and female absorbent articles in a relaxed state of the array is adapted to each specific gender.

Each absorbent article in the array may comprise a second acute angle defined by a third line running through the lowermost point of the side seam and a point along the front leg edge at a distance of 5 cm from the lowermost point of the side seam in the transverse direction X with the article in a relaxed state and fourth line running in the transverse direction X, wherein the second acute angle of each of the first and second size absorbent articles is larger than the second acute angle of each of the third and fourth size absorbent articles.

The front and back panels of each absorbent article in the array may be made of individual parts that are mutually interconnected by means of the absorbent insert, or the front and back panels are integral parts of a single-piece chassis made of one piece of web material having cut-out leg openings, wherein the absorbent body is located overlapping a crotch portion of the chassis. Having a dual-piece chassis requires less chassis material and enables reduced cost, but a one-piece chassis may be deemed more secure due to lack of critical adhesive joints and provide a more underwear-like appearance.

The absorbent articles in the array may be pant diapers or sanitary pants or incontinence pants.

The disclosure further relates to an array of packages comprising the array of disposable pant-type gender-specific absorbent article, wherein the first subarray of absorbent articles includes a plurality of first size absorbent articles adapted for female users and packed in a first package, and a plurality of second size absorbent articles adapted for female users and packed in a second package, wherein the second subarray of absorbent articles includes a plurality of third size absorbent articles for male users and packed in a third package, and a plurality of fourth size absorbent articles adapted for male users and packed in a fourth package, wherein each of the first to fourth packages in the array of packages comprises an external marking indicating the size and/or suitable gender of the disposable pant-type absorbent articles therein. Having a stack of gender-specific and size-specific absorbent articles of an array of gender-specific absorbent articles packed in individual packages and marked with external marking indicating the size and/or suitable gender enables a user simplified selection of an appropriate type of absorbent article out of a plurality of packages comprising different sizes and suitable genders.

BRIEF DESCRIPTION OF THE DRAWINGS

In the detailed description below reference is made to the following figure, in which

FIG. 5-7 show example embodiments of the absorbent article having various first and second acute angles;

FIG. 8 shows an array of packages of absorbent articles according to the disclosure.

DETAILED DESCRIPTION OF PARTICULAR EMBODIMENTS

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure.

Figure 1A:
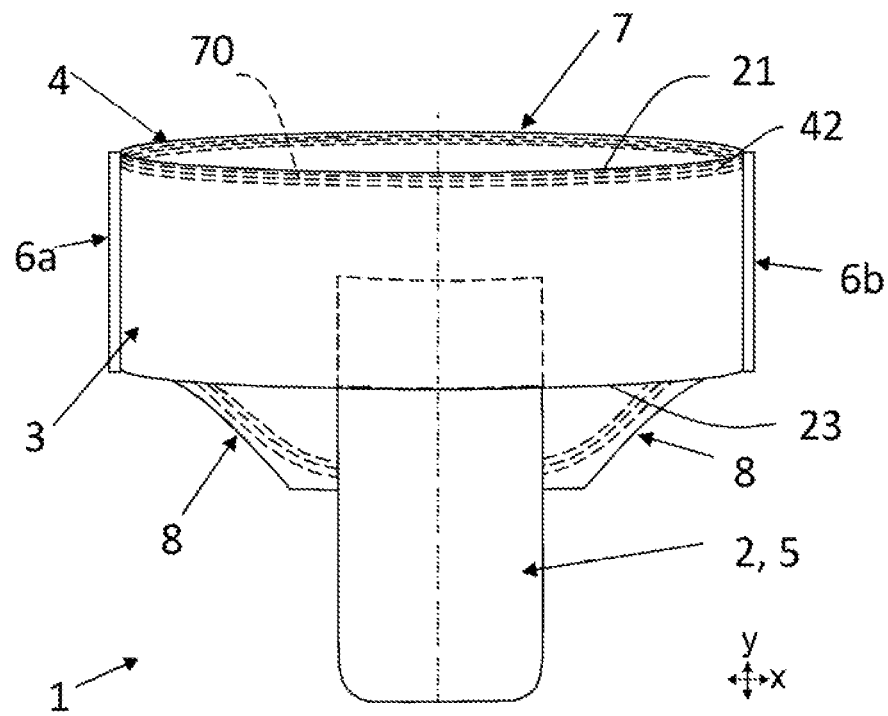
FIG. 1a shows a front view of an example absorbent article with dual-piece chassis.

In FIG. 1a of the drawings an example embodiment of a disposable pant-type absorbent article 1 is schematically illustrated in an assembled and ready-to-use state. The pant-type absorbent article 1 is for example pant diaper, a sanitary pant or an incontinence pant adapted for use of an adult female or male user. The pant-type absorbent article 1 according to the example embodiment of FIG. 1 has a longitudinal direction Y and a transverse direction X and comprises a dual-piece chassis having a front panel 3, a back panel 4 and an absorbent insert 2 located mainly in a crotch portion of the absorbent article 1 and connected to interior side of the front and back panels 3, 4 for bridging the gap between the front and back panels 3, 4. The absorbent insert 2 comprises an absorbent core 5 for absorbing body fluid.

Figure 1B:
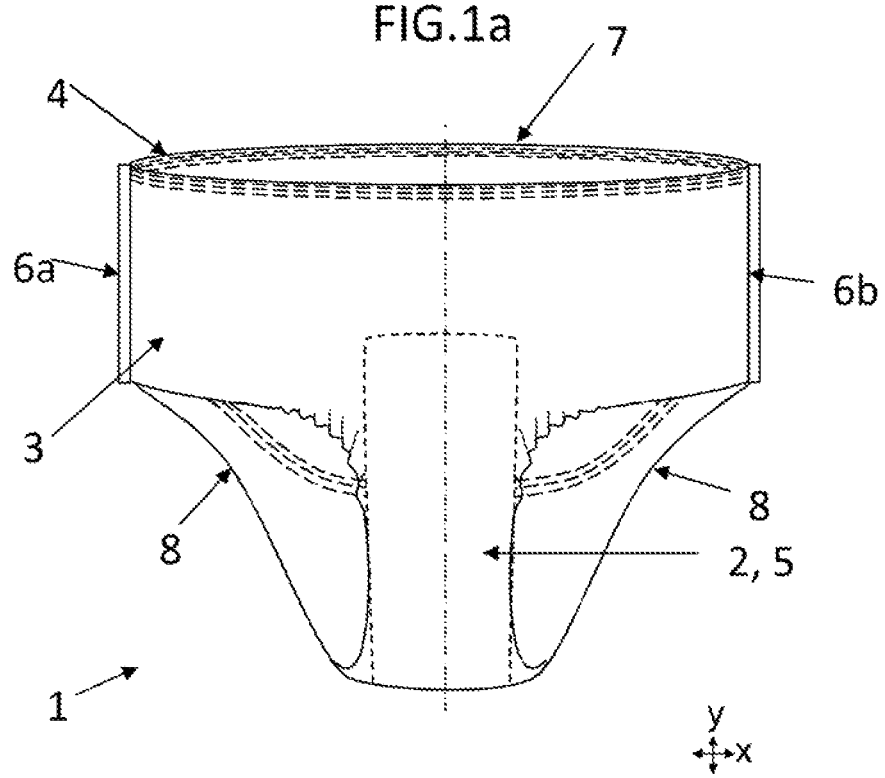
FIG. 1b shows a front view of an example absorbent article with a single-piece chassis.

In FIG. 1b of the drawings a second example embodiment of a disposable pant-type absorbent article 1 specially adapted for an adult female or male user is schematically illustrated in an assembled and ready-to-use state. The difference between the absorbent articles in FIGS. 1a and 1b is that the absorbent article 1 in FIG. 1b has a one-piece chassis, i.e. the front and back panels 3, 4 belong to the same one-piece web material that has an integrally formed crotch region interconnecting the front and back panels 3, 4. The one-piece web material can comprise a single web material or a plurality of different web materials attached side by side along longitudinal edges comprising different materials forming a continuous web in a cross-direction in a diaper production line.

The elastic laminate of the front body panel 3 in the example embodiment of FIG. 1*a* comprises an elastic film sandwiched between two fibrous outer layers and extending in the longitudinal direction Y from a front leg edge 23 to a waist edge 21, and with additional elastic threads 70 attached at a waist portion 42. The elastic laminate of the back body panel 4 may have the same structure.

The elastic laminate of the front and back body panels 3, 4 in the example embodiment of FIG. 1*b* may have the same structure as the those described with reference to FIG. 1*a* but extending slightly longer down towards the crotch region of the article.

In short, manufacturing of the pant-type absorbent article 1 having a dual-piece chassis may for example be performed by first manufacturing two parallel continuous strips of laminated elastic web material that should form the front and rear body panels 3, 4 of the finished absorbent article 1.

Manufacturing of the laminated elastic web material of the front and rear body panels 3, 4 may for example be performed by feeding a first and a second continuous substantially non-elastic sheet of web material, such as for example a substantially non-elastic nonwoven material, along a machine direction, while simultaneously feeding an elastic feature, such as plurality of continuous elastic threads arranged parallel with one another and/or an elastic film material, wherein the elastic film material may be an elastic polymer film or an elastic nonwoven. Subsequently, the first and second sheets of web material are joined to each other with the elastic feature located between the first and second sheets.

The term elastic film herein refers to an elastic material, such as an elastic polymer film or elastic nonwoven, having a continuous one-piece elastic layer extending both in cross direction and longitudinal direction within an elastic area.

The elastic threads and/or elastic film material are attached to the first and second sheets in a tensioned state and parallel with the web material. The elastic threads and/or elastic film material may for example have adhesive applied thereto before being fastened in a tensioned state to the web material. Alternatively, the web material itself may have adhesive applied to it for securing the elastic threads and/or elastic film material thereto. The latter is particularly advantageous when the elastic threads exhibit a curved orientation over the transverse length of the absorbent article 1. The finished laminated elastic web will consequently gather when allowing the elastic threads and/or elastic film material to return to their natural state.

Depending on the desired shape of the final absorbent article the web material may be cut to provide a more underwear-like appearance when assembled into a pant configuration.

While still keeping the elastic threads and/or elastic film in tensioned state the method further comprises a step of placing a finished absorbent insert 2 in the gap between the two parallel continuous strips of laminated elastic web, such that the absorbent insert 2 partly overlaps with the both said strips, and subsequently securing the absorbent insert 2 to said strips. The absorbent insert 2 is thus manufactured separately from the front and back panels 3, 4 and subsequently placed and fastened to said body panels 3, 4 in a suitable manufacturing step.

The manufacturing method may optionally include the step of providing a flat front and/or flat back design. This would involve the step of deactivating the elastic threads and/or elastic film in a central area of the front and/or rear body panel, such that the laminated web material located in the central portion of the front and/or rear body panel 3, 4 may return to a natural un-tensioned state, thereby creating a flat area at a desired region of the front and/or rear body panel 3, 4.

Deactivation of tensioned elastic threads may be performed by keeping a central area of the front and/or rear body panel free of adhesive and subsequently performing an interrupting operating of the elastic threads located in the central portion of the front and/or rear body panel, such that the non-adhered portion of the elastic threads located in the central portion of the front and/or rear body panel 3, 4 are allowed to return to their natural, un-tensioned, state without exerting a gathering effect on the surrounding web material, thereby creating a flat area at a desired region of the front and/or rear body panel 3, 4. One way of deactivating elastic threads is disclosed in application No PCT/SE2016/051221.

Deactivation of a pre-laminated elastic web material comprising an elastic film within a selected area may for example be performed by heating, freezing, cutting or chemically or ultrasound treating the elastic web material within the area concerned, such that the elastic film loses its crimping effect and the laminated web material located in the central portion of the front and/or rear body panel 3, 4 may return to a natural un-tensioned state, thereby creating a flat area at a desired region of the front and/or rear body panel 3, 4.

Such a flat area is typically desirable in the area where the absorbent core 5 overlaps the front and/or rear body panels 3, 4 because the gathering effect of active elastic threads/film on the absorbent core 5 may be deemed having a negative effect on the absorption capacity of the absorbent core 5. The elastic means in the lower area of the front section may also have been deactivated similarly.

After securing the absorbent insert 2 to the two parallel continuous strips of laminated elastic web the entire continuous material band is folded at a fold line extending substantially in the transverse direction X of the absorbent insert 2, such that the two parallel continuous strips of laminated elastic web becomes superposed after folding. Thereafter the two parallel continuous strips of laminated elastic web are joined to each other at discrete locations at predetermined fixed intervals along the material band using for example ultrasonic welding, to form side seams 6*a*, 6*b* of the finished absorbent article 1. Consequently, side edges of the front panel 3 are permanently attached to opposite side edges of the back panel 4 to form side seams 6*a*, 6*b* of the finished and assembled absorbent article 1, thereby also defining a waist-opening 7 and a pair of leg-openings 8.

In a final step the continuous material band is cut in a machine cross direction in the area in or adjacent to the side seams 6*a*, 6*b* to transform the folded continuous material band into individual absorbent articles 1. When the laminated elastic web material of the front and back panels 3, 4 is no longer held in stretched state in the transverse direction X the sandwiched elastic threads/film will cause the web material to gather, i.e. to contract in the transverse direction X and to form small undulations in the laminated elastic web material. An example manufacturing process for such an elastic web material is described more in detail in document WO 2014/098683 A1, which is referred to in its entirety.

More specifically, the elastic laminate used as front and/or back panels 3, 4 in the pant-type absorbent article may comprise at least three layers, viz. first and second outer nonwoven layers which are chosen so that they, in combination with an inner elastic film layer, give the elastic laminate high resistance to puncture, in order to prevent penetration by finger nails for example. The first and second outer nonwoven layers also provide a soft and cloth-like feel to the laminate. Examples of suitable materials are carded webs and spunbond materials. In certain embodiments, the basis weight of the fibrous material of the first and second outer nonwoven layers should be between 8 and 35 g/m$^2$, preferably between 10 and 30 g/m$^2$, more preferably between 12 and 25 g/m$^2$. Non-limiting examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibres of different polymers is also possible. The nonwoven layers should be chosen so that the tensile strength of the laminate will be sufficient for the intended purpose.

In certain embodiments, the elastic film preferably has a basis weight between 20 and 80 g/m$^2$, preferably between 20 and 60 g/m$^2$. The elastic film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. In certain embodiments, the total basis weight of the elastic laminate is preferably between 40 and 100 g/m$^2$, more preferably not more than 90 g/m$^2$.

As described above, the elastic laminate may be composed of first and second outer layers of fibrous material and an elastic film located between said fibrous layers. The elastic laminate may also comprise one or more additional fibrous layers laminated to one or both of the first and second fibrous layers. Such additional fibrous layers may be present only in parts of the elastic laminate. Thus the elastic laminate need not be identical all over its area, but may comprise different layers in different areas.

The first and second outer layers of fibrous material can be bonded to the elastic film layer while this is in a stretched state, so called stretch-bonding. The resulting laminate will be elastically stretchable. The film can be bonded to nonwoven layers in an un-stretched condition. Such laminate then may need further treatment in form of mechanical activation which tear the nonwoven layers if the nonwoven is inelastic.

The elastic film can be an apertured elastic film and the apertures can be premade or the apertures formed in an ultrasonic bonding process or heat welding process at or near the bond sites in which the bonding process creates holes in the film and or the nonwoven layers. Holes can also be formed outside the bond sites when to the film is applied in stretch condition between the nonwoven layers, a method of creating such laminate is described in WO 2013 002691

In certain embodiments, the open area of the elastic film layer is preferably at least 5%, more preferably at least 8%. The open area is measured by image analysis methods and is defined as the sum of the hole area divided by the total area of the film sample.

Another method for manufacturing an elastic laminate is described in WO 03/047488, wherein one spunbond layer is applied to the film, said film being in a tacky state and will thus bond to the spunbond layer, while the other spunbond layer is adhesively laminated to the film layer, using for example a pressure sensitive hot melt adhesive. Alternatively, the laminate is manufactured according to a modified version of this method, wherein the modification involves that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

In an alternative embodiment the laminate is manufactured by feeding a first fibrous layer in the form of a nonwoven web into a bonding nip and extruding a molten elastic film-forming polymer through a die into the nip. The first fibrous layer and the elastic film form a first laminate. In a second lamination step the film side of the first laminate is coated or sprayed with adhesive and is subsequently passed through a second bonding nip together with a second fibrous layer to form the laminate. The laminate is subsequently activated by subjecting it to incremental stretching.

Another method of producing a suitable laminate is described in WO 2007133127, wherein a bi-laminate of an elastic film and a nonwoven has been activated by mechanically stretching. The activated bi-laminate is stretched and bonded to a second nonwoven layer forming a three layer laminate.

In certain embodiments the elastic laminate material is preferably arranged as an outside coversheet material as well as inner coversheet material over at least part of the front portion, back portion and connecting portion of the chassis. In certain embodiments, the elastic laminate material may constitute the sole component of the chassis in at least 20%, preferably at least 25%, more preferably at least 30% and most preferably at least 40% of the total surface area of the article, as seen in a flat state.

The elastic laminate may be absent in a substantial part of the connecting portion of the article. A crotch panel material may underlie at least part of the absorbent assembly on the garment-side thereof. The crotch panel material may be of a non-elastic web material, although elastic materials may also be used. Suitably, the crotch panel material is a nonwoven material. The crotch panel material is joined to the elastic laminate along seams.

Figure 2:
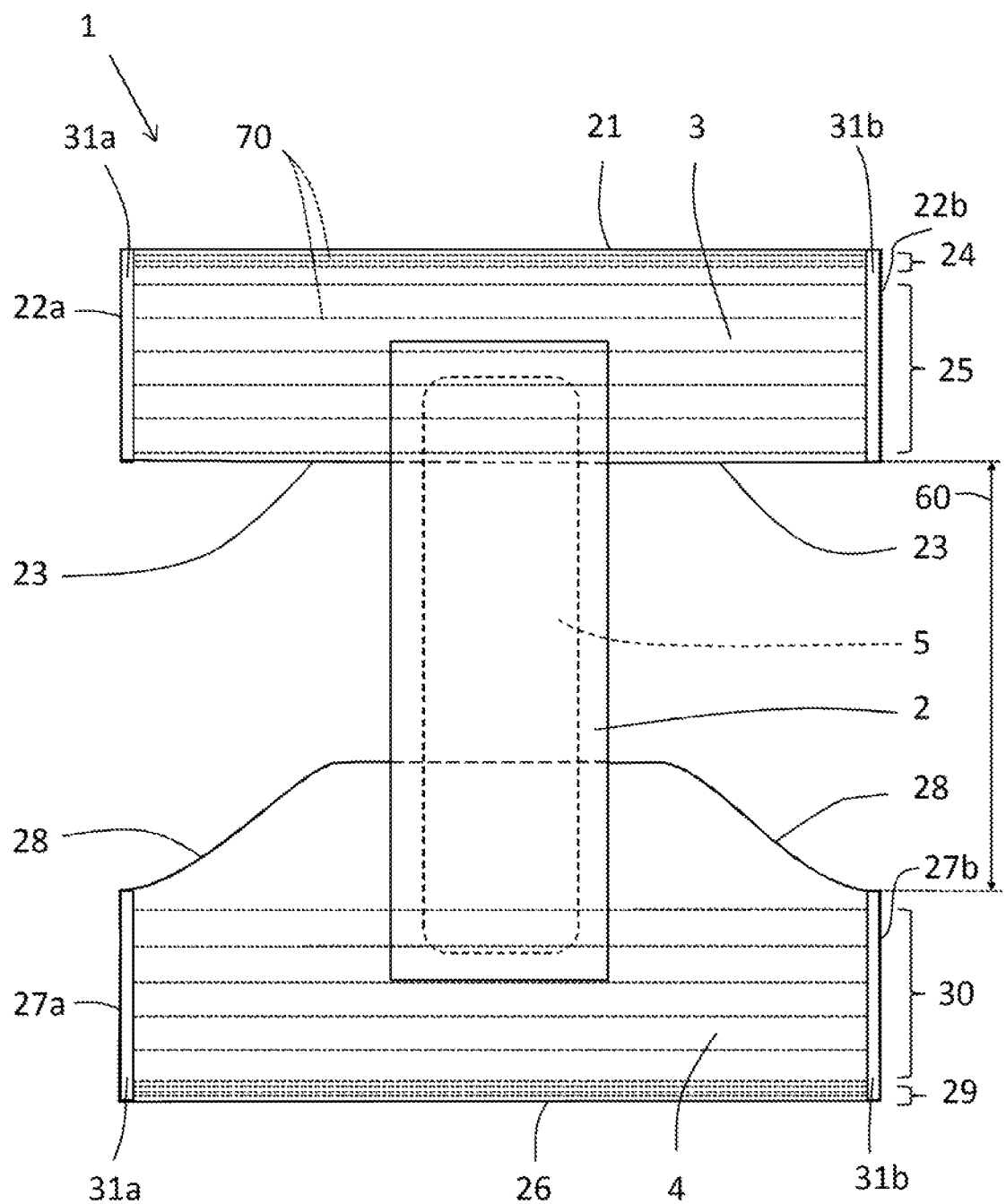
FIG. 2 shows an example absorbent article in a flat and disassembled state.

FIG. 2 schematically shows an example embodiment of the absorbent article according to the disclosure with the side seams 6a, 6b in a disassembled state, i.e. where the side seams has been opened, or in a state where no side seams were produced. The front panel 3 comprises a waist edge 21, a left side edge 22a, a right side edge 22b and a front leg edge 23.

The laminated web material of the front panel 3 may for example comprise a first at least partly elastic region 24 extending between the left and right side edges 22a, 22b primarily in the transverse direction X and being located adjacent the front panel waist edge 21, thereby defining a waist elastic feature.

The laminated web material of the front panel 3 further comprises a second at least partly elastic region 25 located next to the first at least partly elastic region 24 on the side of the front leg edge 23. The second at least partly elastic region 25 may be referred to as an elastic belly region because it may, depending on the size of the second at least partly elastic region 25, extend over the belly of a user.

The front panel may further have a leg elastic feature (not shown) extending between the left and right side edges 22a, 22b primarily in the transverse direction X and being located adjacent the front leg edge 23.

The back panel 4 comprises a waist edge 26, a left side edge 27a, a right side edge 27b and a back leg edge 28.

The laminated web material of the back panel 4 may for example comprise a third at least partly elastic region 29 extending between the left and right side edges 27a, 27b primarily in the transverse direction X and being located adjacent the back panel waist edge 26, thereby defining a waist elastic feature.

The laminated web material of the back panel 4 may further comprise a fourth at least partly elastic region 30 located next to the third at least partly elastic region 29 on the side of the back leg edge 28.

The back panel may further have a leg elastic feature (not shown) extending between the left and right side edges 27a, 27b primarily in the transverse direction X and being located adjacent the back leg edge 28.

An absorbent insert 2 is located mainly in a crotch portion of the absorbent article 1 and being connected to the front and back panels 3, 4 and having an absorbent core 5.

The example embodiment absorbent article of illustrated in FIG. 2 comprises an elastic laminate having elastic threads in both the waist and body portion. The first at least partly elastic region 24 of the front panel 3 may for example comprise a plurality of elastic threads 70 arranged in parallel at substantially equally spaced intervals of 2 to 8 millimetres and for example comprise 4 to 6 elastic threads. Each of the elastic threads 70 may have substantially equal mass density, which for example may lie in the range 600 to 1200 decitex, specifically in the range of 750 to 1000 decitex.

The second at least partly elastic region 25 of the front panel 3 typically corresponds to the belly portion of the absorbent article 1 and may for example comprise a plurality of elastic threads 70 arranged parallel at substantially equally spaced intervals of 5 to 13 millimetres and may for example comprise 9 to 27 elastic threads. Each of the elastic threads 70 may have substantially equal mass density, which for example may lie in the range 350 to 900 decitex, specifically in the range of 500 to 700 decitex. Having relatively large intervals between neighbouring elastic threads in a belly portion in relation to the lower area of the front panel 3 enables a large and comfortable belly portion.

The third at least partly elastic region 29 of the back panel 4 may for example comprise a plurality of elastic threads 70 arranged parallel at substantially equally spaced intervals of 2 to 8 millimetres and may for example comprise 4 to 6 elastic threads. Each of the elastic threads 70 may have substantially equal mass density, which for example may lie in the range 600 to 1200 decitex, specifically in the range of 750 to 1000 decitex.

The fourth at least partly elastic region 30 of the back panel 4 may for example comprise a plurality of elastic threads 70 arranged parallel at substantially equally spaced intervals of 5 to 13 millimetres and may for example comprise 9 to 27 elastic threads. Each of the elastic threads 70 may have substantially equal mass density, which for example may lie in the range 350 to 900 decitex, specifically in the range of 500 to 700 decitex.

In case the same type and size of threads, such as for example 940 dtex, is used for waist elastics for both the male and female product a suitable example elongation for the male can be in the range of 75-100% and a suitable example elongation for the female can be in the range of 150-250%. The higher level of elongation of the elastic threads of the female waist elastics compared with the male waist elastics results in a higher degree of gathering effect in the female articles, thereby adapting the shape of the absorbent article to better fit each specific gender.

In case the side seams 6a, 6b are free from adhesive the continuous elastic threads 70 will in the area of the side seam 6a, 6b during manufacturing of the absorbent article 1 snap back upon the cutting operation required for splitting the continuous material band into individual absorbent articles. Consequently, a narrow longitudinal strip 31a, 31b of material is illustrated having no elastic threads 70 attached thereto in the example embodiment of FIG. 2.

The shape of the front and back panel 3, 4 may be varied. For example, one or both of the front panel and the back panels 3, 4 may have a substantially rectangular shaped panel. Moreover, any elasticised regions of the front and/or back panels 3, 4 may have curved portions adapted to a curved shape of for example a leg edge.

As described above, one objective with the present disclosure is to provide an array of gender-specific absorbent articles in at least two sizes, for the purpose of providing absorbent articles with increased comfort and fit as well as discrete underwear-like visual appearance, while taking into account anatomical differences between men and women and the need for individual sizes, and while also maintaining a low manufacturing cost. The present disclosure provides a solution wherein the degree of gathering of the sheet material of the front and/or back panel in the transverse direction X is used for adapting absorbent articles to have a better fit for each specific gender, while using the same geometry and dimension of the front and back panels 3, 4 in an extended state.

Consequently, both absorbent articles specifically adapted for male and female users can be manufactured with a minimum of change of the production line, namely merely by adapting features influencing the degree of gathering effect. The degree of gathering effect can for example be adapted by increasing or decreasing the level of elongation of the elastic threads and/or elastic film at the moment of attachment to the sheet material of the front and back panels, or by increasing or decreasing the mass density of the elastic means used for elasticising the front and back panels, such as elastic threads and/or elastic film, or by increasing or decreasing a distance between neighbouring elastic threads in the front and back panel, or by increasing or decreasing the stiffness of the sheet material forming the front and back panel. As a result, cost-efficient manufacturing of an array of gender-specific absorbent articles is made possible by using the essentially the same size of the front and back panels in a non-elasticised or extended state while using the level of gathering effect of the sheet material of the front and back panels for adapting the shape of the absorbent article to better fit each specific gender.

Figure 3:
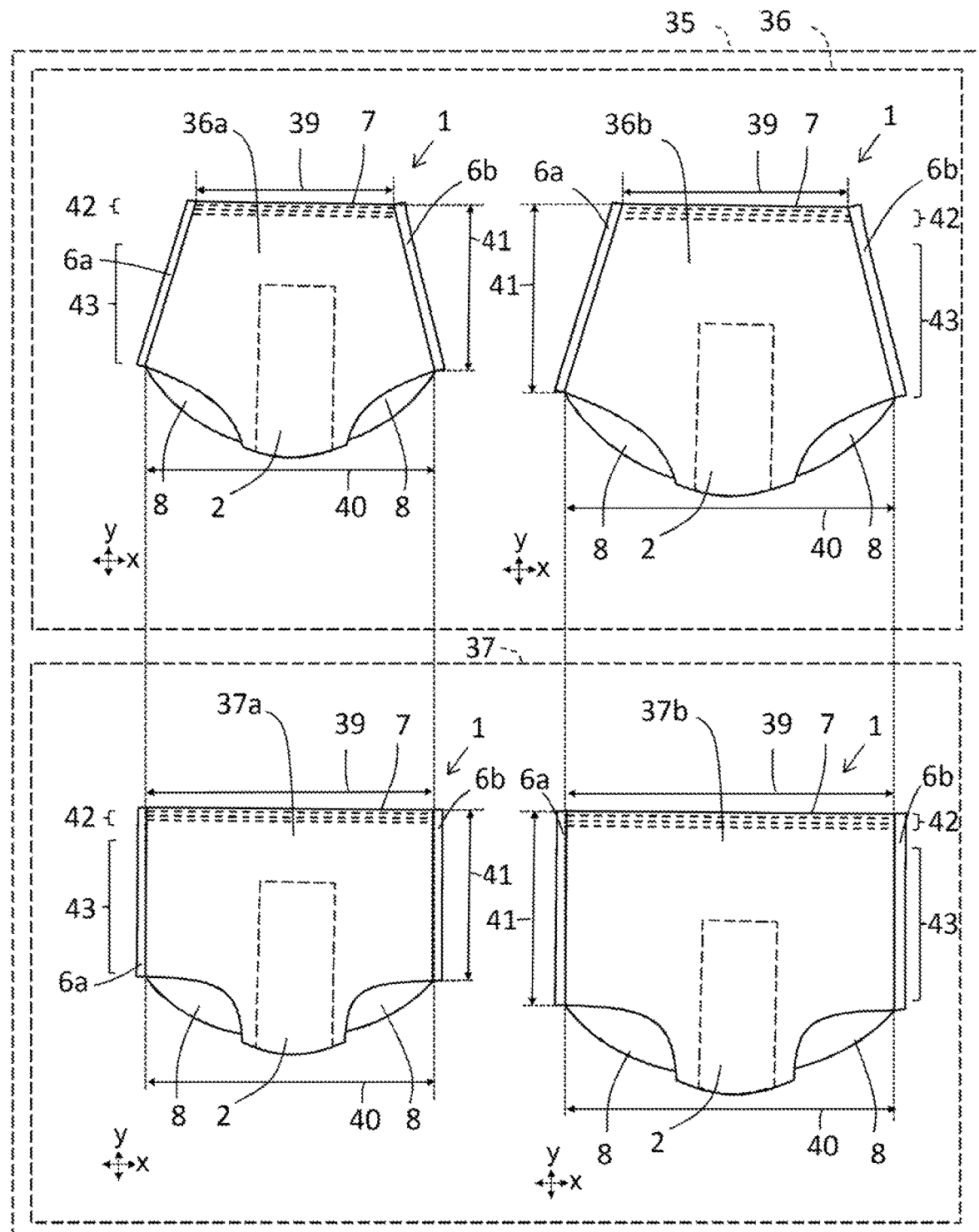
FIG. 3 shows an array of absorbent articles of various sizes of the first and second subarrays in a relaxed state.
Figure 4:
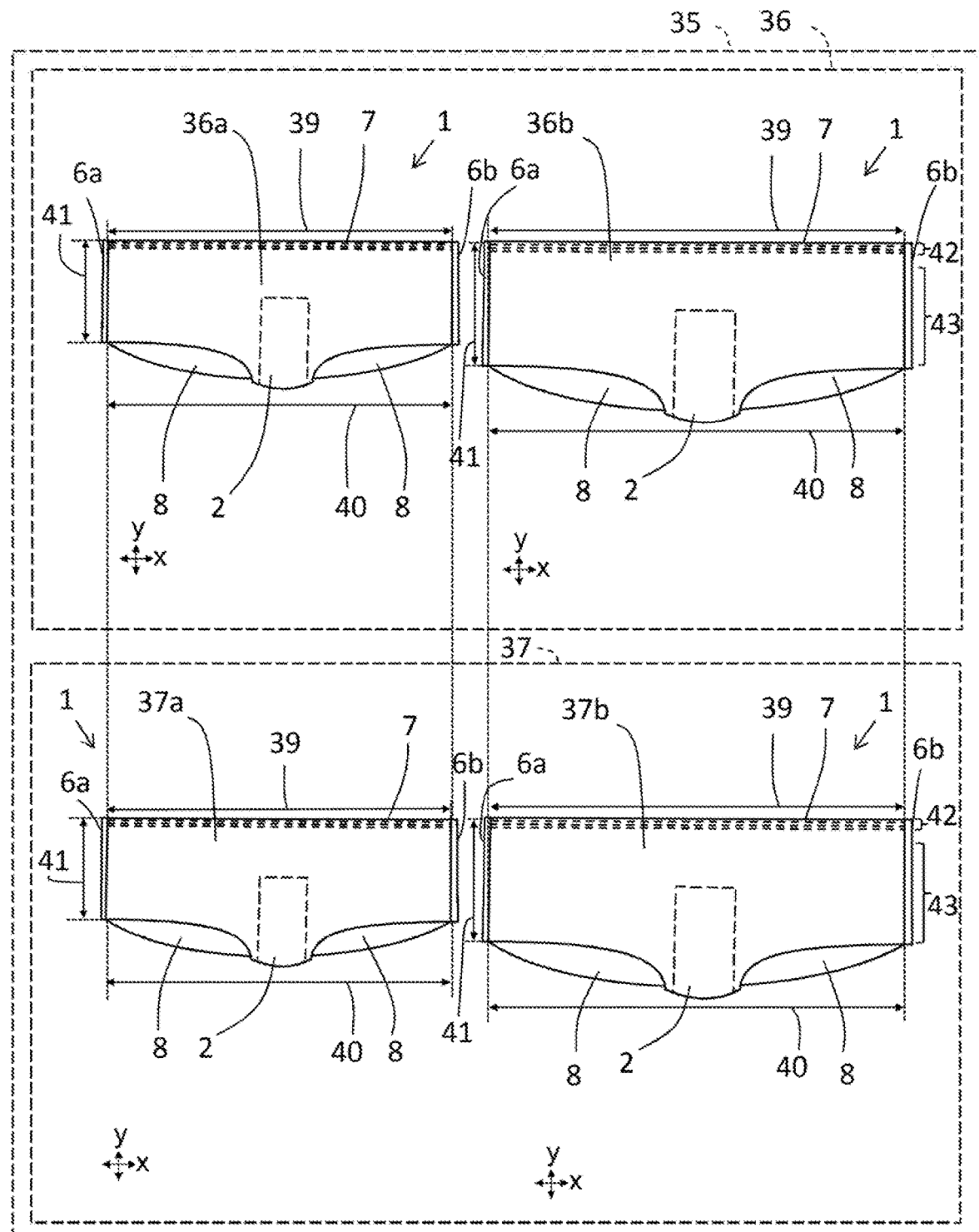
FIG. 4 shows an array of absorbent articles of various sizes of the first and second subarrays in an extended state.

The array of disposable pant-type gender-specific absorbent articles adapted for female and male users according to the disclosure is described more in detail below with reference to FIGS. 3 and 4, wherein FIG. 3 schematically shows an example embodiment of an array 35 of disposable pant-type gender-specific absorbent articles 1 adapted for female and male users in a relaxed, natural, state, and FIG. 4 schematically shows the array 35 of the example embodiment of FIG. 3 in an extended state.

The example array 35 of FIGS. 3 and 4 comprises a first subarray 36 of absorbent articles 1 including a first size absorbent article 36a adapted for female users and a second size absorbent article 36b adapted for female users, and a second subarray 37 of absorbent articles 1 including a third size absorbent article 37a for male users and a fourth size absorbent article 37b adapted for male users.

The first and third elastic regions 24, 29 of the front and back panels 3, 4 of each absorbent article in the array 35 jointly define a transversely elasticised waist portion 42 of the absorbent article 1 in an assembled and ready to use state.

The length of the waist portion in the longitudinal direction Y may be in the range of 5-75 millimetres, specifically in the range of 10-50 millimetres, as measured in a relaxed state of the absorbent article 1.

The second and fourth elastic regions 25, 30 of the front and back panels 3, 4 of each absorbent article in the array 35 jointly define a transversely elasticised body portion 43 of the absorbent article 1 in an assembled and ready to use state.

A distance between the waist portion 42 and the body portion may for example be less than 20 millimetres, specifically less than 10 millimetres.

The absorbent articles of the array may further include a leg elastic feature (not showed) of the front and back panels 3, 4.

The elastic laminate of each of the front and back body panels 3, 4 of the absorbent articles in the array shown in FIGS. 3 and 4 comprises an elastic film extending in the longitudinal direction Y from the leg edge to the waist edge and with additional elastic threads attached at the waist portion 42.

Alternatively, the elastic laminate of each of the front and back body panels 3, 4 of the absorbent articles 1 in the first subarray 36 may comprise an elastic film extending in the longitudinal direction Y from the leg edge to the waist edge and with additional elastic threads attached at the waist portion 42, wherein the elastic laminate of each of the front and back body panels 3, 4 of the absorbent articles 1 in the second subarray 37 may comprise an elastic film extending in the longitudinal direction Y from the leg edge to the waist edge and without additional elastic threads attached at the waist portion 42. By having additional elastic threads attached at the waist portion to the absorbent articles of only the first subarray (female articles) the female articles may be provided with their characteristic shape of a relatively narrow hip and wider body.

The second size is larger than the first size, and the fourth size in larger than the third size. The difference in size may for example be reflected in increased circumferential length of the waist portion 42 in a relaxed state. The term circumferential length of any portion of the absorbent article herein refers to the inner circumferential length of said portion of the absorbent article. The circumferential length of the waist portion 42 in a relaxed state typically corresponds to twice the length 39 between the inner sides of the upper end of the side seams 6a, 6b, when the absorbent article is measured in flat state, as schematically illustrated in FIG. 3.

The difference in size may alternatively, or in combination with above, for example be reflected in increased height 41 of the side seams 6a, 6b in the longitudinal direction Y, as schematically illustrated in FIGS. 3 and 4.

According to an example embodiment, each absorbent article 1 within the first and/or second subarray 36, 37 may have identical absorbent inserts 2 and absorbent cores 5 for further reducing manufacturing costs.

Moreover, as illustrated in FIG. 2, a smallest longitudinal distance 60 between a side edge 22b of the front panel 3 and an oppositely located side edge 27b of the back panel 4, as measured with disassembled side seams 6a, 6b, or prior to producing the side seams, of each absorbent article 1 in the array 35 may be essentially the same. This enables further reduced manufacturing costs because this enables use of more common manufacturing equipment and the use of a common absorbent insert.

As described above with reference to FIGS. 1a, 1b and 2-4 each absorbent article of the array has a longitudinal direction Y and a transverse direction X and comprises a front panel 3 having a waist edge 21 and a pair of side edges 22a, 22b, and a back panel 4 having a waist edge 26 and a pair of side edges 27a, 27b. In FIG. 3 the absorbent articles 1 of the array 35 are illustrated in a front view in a relaxed state and being in a substantially flat condition. The front and back panels 3, 4 are joined to each other at opposite side edges 22a, 27a, 22b, 27b by side seams 6a, 6b forming a waist opening 7 and two leg openings 8. Each absorbent article 1 in the array 35 comprises a transversely elasticised waist portion 42 extending along the waist opening 7.

In order to accomplish an array 35 of gender-specific absorbent articles 1 in at least two sizes with increased comfort and fit as well as discrete underwear-like visual appearance, while taking into account anatomical differences between men and women and the need for individual sizes, and while also maintaining a low manufacturing cost, at least one of said first and second size absorbent articles 1 has a first circumferential length of the waist portion 42 in a relaxed state and a second circumferential length of the waist portion 42 in an extended state, and at least one of said third and fourth size absorbent articles 1 has a third circumferential length of the waist portion 42 in a relaxed state and a fourth circumferential length of the waist portion 42 in an extended state, wherein the circumferential length of the waist portion 42 in the relaxed state is measured according to the method described below with a tension of 3 Newton, and the circumferential length of the waist portion 42 in the extended state is measured according to the method described below with a tension of 80 Newton, wherein the third circumferential length is more than 10%, specifically more than 15% larger than the first circumferential length, and the fourth circumferential length is less than 5%, specifically less than 3%, larger than the second circumferential length.

This essentially means that at least one absorbent article of each subarray 36, 37 shares essentially the same geometry and dimension of the front and back panels 3, 4 in an extended state for the purpose of accomplishing reduced manufacturing cost, while at least one absorbent article of each subarray 36, 37 still has a shape and form in a relaxed state that is adapted to specifically fit a unique gender.

It is well-known that the shape of male hips are relatively narrow and has a certain resemblance with a box-shape, i.e. with relatively vertically oriented hip sides, whereas the shape of female hips are relatively wide and has a certain a resemblance with a trapezoid-shape, i.e. with more inclined hip sides. Consequently, by setting the first circumferential length smaller than the third circumferential length, as defined above, a least one absorbent article of the first subarray 36 has a shape and form in a relaxed state that is specifically adapted to fit a female user, and at least one absorbent article of the second subarray 37 has a shape and form in a relaxed state that is specifically adapted to fit a male user.

As stated above, the fourth circumferential length is less than 5%, specifically less than 3%, larger than the second circumferential length. Manufacturing of various types and sizes of absorbent articles on a single manufacturing line requires a certain degree of adaption of the manufacturing line, such as for example taking into account absorbent article specific sizes. The resulting circumferential length of the waist portion 42 of an absorbent article in an extended state is generally directly dependent on the selected width of the front and back panels 3, 4 of the absorbent article, in case side seam geometry remains constant. The width of the front and back panels 3, 4 in extended state is consequently an important manufacturing parameter and by using substantially the same width for two different articles in the array 35 the manufacturing process typically enables simplified manufacturing due to reduced need for adjustment of the manufacturing line for each individual type of absorbent article, and the use of a larger level of identical manufacturing equipment.

Having at least one absorbent articles of each subarray 36, 37 sharing essentially the same width dimension of the front and back panels 3, 4 can for example be defined in terms of circumferential length of the waist portion 42 and/or body portion 43 in an extended state.

The circumferential length of the waist portion 42 in an extended state typically corresponds to twice the length 39 between the inner sides of the upper end of the side seams 6a, 6b, when the absorbent article is held in an extended state, as schematically illustrated in FIG. 4.

Moreover, the circumferential length of the body portion 43 in an extended state typically corresponds to twice the length 40 between the inner sides of the lower ends of the side seams 6a, 6b, when the absorbent article is held in an extended state, as schematically illustrated in FIG. 4.

With reference to FIG. 4, the circumferential length of the waist portion 42 in an extended state of the first size absorbent article 36a is smaller than a circumferential length of the waist portion 42 in an extended state of the second size absorbent article 36b. The second size absorbent article 36b is thus larger than the first size absorbent article 36a.

With reference to FIG. 4, the circumferential length of the waist portion 42 in an extended state of the third size absorbent article 37a is smaller than a circumferential length of the waist portion 42 in an extended state of the fourth size absorbent article 37b. The fourth size absorbent article 37b is thus larger than the third size absorbent article 37a.

According to an example embodiment of the array 35 according to the disclosure, and as illustrated in FIG. 4, a circumferential length of the waist portion 42 in an extended state of the first size absorbent article 36a is substantially equal with a circumferential length of the waist portion 42 in an extended state of the third size absorbent article 37a.

Moreover, according to a further example embodiment of the array according to the disclosure and as illustrated in FIG. 4, a circumferential length of the waist portion 42 in an extended state of the second size absorbent article 36b is substantially equal with a circumferential length of the waist portion 42 in an extended state of the fourth size absorbent article 37b. By having both the smaller and larger absorbent articles of each subarray 36, 37 sharing essentially the same circumferential length of the waist portion 42 in an extended state, even further manufacturing cost savings are possible due to increased number of absorbent articles sharing dimensional size.

A certain level of dimensional variation of the circumferential length of the waist portion 42 in extended state will always occur due to small variations caused by manufacturing variations and tolerances of the front and back panel cutting process and/or side seam manufacturing process of individual absorbent articles. Moreover, variations of the elastic tensile stress caused by the waist elastic feature may also cause dimensional variation of the circumferential length of the waist portion 42 in extended state because the circumferential length of the waist portion 42 in extended state is measured when waist portion 42 of the absorbent article is transversally extended with a predetermined force level. Consequently, manufacturing and material-caused dimensional variation of the circumferential length of the waist portion 42 in extended state of about less than 5%, specifically less than 2%, between different absorbent articles is still being deemed falling under term "substantially equal".

According to an example embodiment of the array 35 according to the disclosure and as illustrated in FIG. 3, the circumferential length of the waist portion 42 in a relaxed state of the first size absorbent article 36a is smaller than circumferential length of the waist portion 42 in a relaxed state of the third size absorbent article 37a. This shows that the degree of gathering of the sheet material of the front and/or back panel in the transverse direction X can be used for adapting the shape and form of absorbent articles to have a better fit for each specific gender.

According to an example embodiment of the array according to the disclosure and as illustrated in FIG. 3, the circumferential length of the waist portion 42 in a relaxed state of the second size absorbent article 36b is smaller than a circumferential length of the waist portion 42 in a relaxed state of the fourth size absorbent article 37b. This shows that the degree of gathering of the sheet material of the front and/or back panel in the transverse direction X can be used for adapting the shape and form of absorbent articles to have a better fit for each specific gender.

As illustrated in FIGS. 1a, 1b, 2-4, each absorbent article 1 in the array 35 may according to an example embodiment of the disclosure, further comprise a transversely elasticised body portion 43 located adjacent to and extending substantially parallel with the waist portion 42. The transversely elasticised body portion 43 typically stretches over a larger area of the front and back panels 3, 4 in the longitudinal direction Y than the waist portion 42.

The circumferential length of the body portion 43 in an extended state typically corresponds to twice the length 39 between the inner sides of the lower ends of the side seams 6a, 6b, as schematically illustrated in FIG. 4.

More in detail, the circumferential length of the body portion 43 in an extended state of the first size absorbent article 36a of the array 35 of the example embodiment of FIG. 4 may be smaller than the circumferential length of the body portion 43 in an extended state of the second size absorbent article 36b. This shows that the second size absorbent article is larger than the first size absorbent article, such that the array of absorbent articles provides improved offer of suitable absorbent articles for the each individual user.

Moreover, the circumferential length of the body portion 43 in an extended state of the third size absorbent article 37a of the array 35 of the example embodiment of FIG. 4 is smaller than the circumferential length of the body portion 43 in an extended state of the fourth size absorbent article 37b. This shows that the fourth size absorbent article is larger than the third size absorbent article, such that the array of absorbent articles provides improved offer of suitable absorbent articles for the each individual user.

Moreover, the circumferential length of the body portion 43 in an extended state of the first size absorbent article 36a of the array 35 of the example embodiment of FIG. 4 is substantially equal with the circumferential length of the body portion 43 in an extended state of the third size absorbent article 37a, and the circumferential length of the body portion 43 in an extended state of the second size absorbent article 36b of the array 35 of FIG. 4 is substantially equal with the circumferential length of the body portion 43 in an extended state of the fourth size absorbent article 37b. This shows that the array comprises four absorbent articles based on only two different basic shapes of the front and back panels 3, 4 in an extended state, thereby enabling reduced manufacturing cost of the array.

Figure 5:
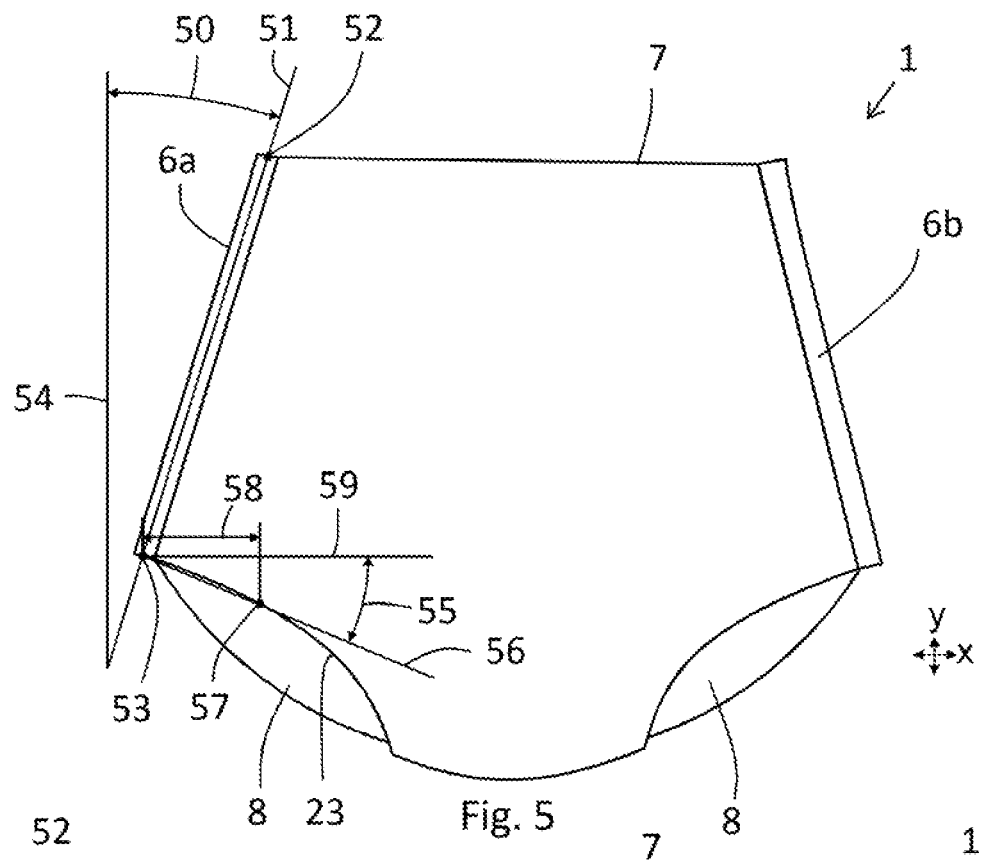
Figure 6:
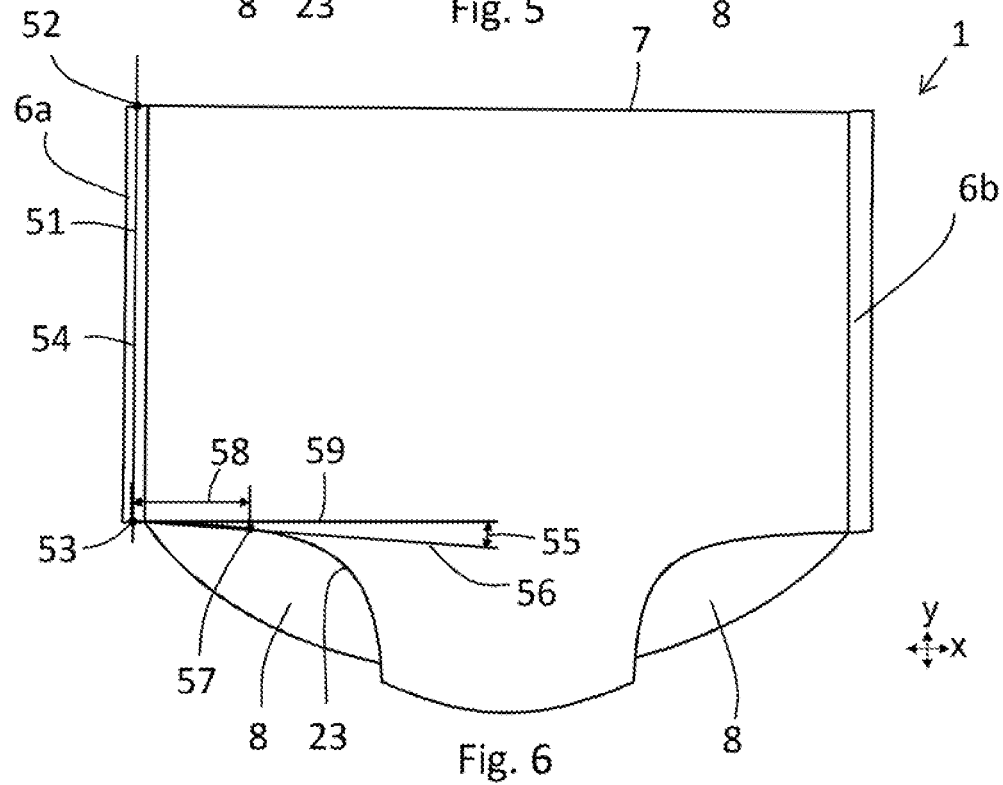

The specific shape and form of male and female absorbent articles of the array of absorbent articles according to the disclosure can be defined in alternative forms. For example, as shown in FIG. 5, a front view of an example absorbent article of the first subarray 36, i.e. an absorbent article adapted for female users, is schematically shown in a relaxed and flat state. The absorbent article 1 comprises a first acute angle 50 defined by a first line 51 extending between an uppermost point 52 of the side seam 6a, 6b and a lowermost point 53 of the side seam 6a, 6b and a second line 54 extending in the longitudinal direction Y. FIG. 6 schematically shows a corresponding view of an example absorbent article of the second subarray 37, i.e. an absorbent article adapted for male users. The first acute angle 50 is larger in the absorbent article 1 of the first subarray 36 than in the absorbent article 1 of the second subarray 37 with the article in a relaxed state. This essentially means that the absorbent article of the first subarray 36, which has a more inclined side seams 6a, 6b in a relaxed state, generally may be deemed being better adapted to fit the relatively wide and more trapezoid-shaped form of the female hips, while the absorbent article of the second subarray 37, which has essentially vertically oriented side seams 6a, 6b in a relaxed state, generally may be deemed being better adapted to fit the relatively narrow and box-shaped form of the male hips.

Consequently, each absorbent article of the array has a shape and form in a relaxed state that is adapted to a better fit for each specific gender, and this is primarily or entirely the result of adapting the degree of gathering of the sheet material of the front and/or back panel in the transverse direction X.

The first acute angle 50 may be substantially equal in the absorbent articles 1 of the first and second subarrays 36, 37 with the article in an extended state.

Moreover, the specific shape and form of male and female absorbent articles of the array of absorbent articles according to the disclosure can be defined in yet more alternative forms. For example, as shown in FIGS. 5 and 6, each absorbent article in the array may comprises a second acute angle 55 defined by a third line 56 running through the lowermost point 53 of the side seam 6a, 6b and a point 57 along the front leg edge 23 at a distance 58 of 5 cm from the lowermost point 53 of the side seam 6a, 6b in the transverse direction X and a fourth line 59 running in the transverse direction X, as measured in a relaxed and flat state of the absorbent article.

When a certain type of pant-type absorbent article is provided with varying degree of gathering level of the waist portion at least two specific features relevant for the fit and comfort of the absorbent article changes. These two specific features are inclination of the side seams 6a, 6b, i.e. essentially corresponding to a change of the first acute angle 50 as defined above, and inclination of the front leg edge 23 of the absorbent article 1. Increased inclination of the front leg edge 23 relative the transverse direction X, i.e. the horizontal direction, is consequently generally associated with increased adaptation to female users.

The second acute angle 55 may be substantially equal in the absorbent articles 1 of the first and second subarrays 36, 37 with the article in an extended state.

In FIGS. 5 and 6 it is clear that the second acute angle 55 is larger in the absorbent article 1 of the first subarray 36 than in the absorbent article 1 of the second subarray 37. Consequently, this essentially means that the absorbent article of the first subarray 36, which has a more inclined front leg edge 23 8 in a relaxed state, generally may be deemed being better adapted to fit the relatively wide and more trapezoid-shaped form of the female hips, while the absorbent article of the second subarray 37, which has less inclined front leg edge 23 in a relaxed state, generally may be deemed being better adapted to fit the relatively narrow and box-shaped form of the male hips.

Consequently, each absorbent article of the array has a shape and form in a relaxed state that is adapted to a better fit for each specific gender, and this is primarily or entirely the result of adapting the degree of gathering of the sheet material of the front and/or back panel in the transverse direction X.

Moreover, as shown in FIG. 7, in some situations it may be desirable to provide the male absorbent articles of the array with the certain trapezoid shape, although typically to a lesser degree than the female absorbent articles of the array. Hence, the first acute angle 50 of the absorbent articles of the second subarray may be larger than zero but still smaller than the first acute angle 50 of the absorbent articles of the first subarray.

As illustrated in FIG. 8, the disclosure also relates to an array of packages 80 comprising the array of disposable pant-type gender-specific absorbent articles 1. The array of packages 80 comprises at least a first package 81, a second package 82, a third package 83 and a fourth package 84. The first package 81 comprises a plurality of first size absorbent articles 1 associated with a first subarray 36 and adapted for female users. The second package 82 comprises a plurality of second size absorbent articles 1 associated with a first subarray 36 and adapted for female users. The third package 83 comprises a plurality of third size absorbent articles 1 associated with a second subarray 37 and adapted for male users. The fourth package 84 comprises a plurality of fourth size absorbent articles 1 associated with a second subarray 37 and adapted for male users. Each of the first to fourth packages 81, 82, 83, 84 in the array of packages 80 comprises an external marking indicating the size and/or suitable gender of the disposable pant-type absorbent articles 1 therein. Such an array can for instance be found in a supermarket or a grocery store selling absorbent articles.

Experimental Data

Figure 9:
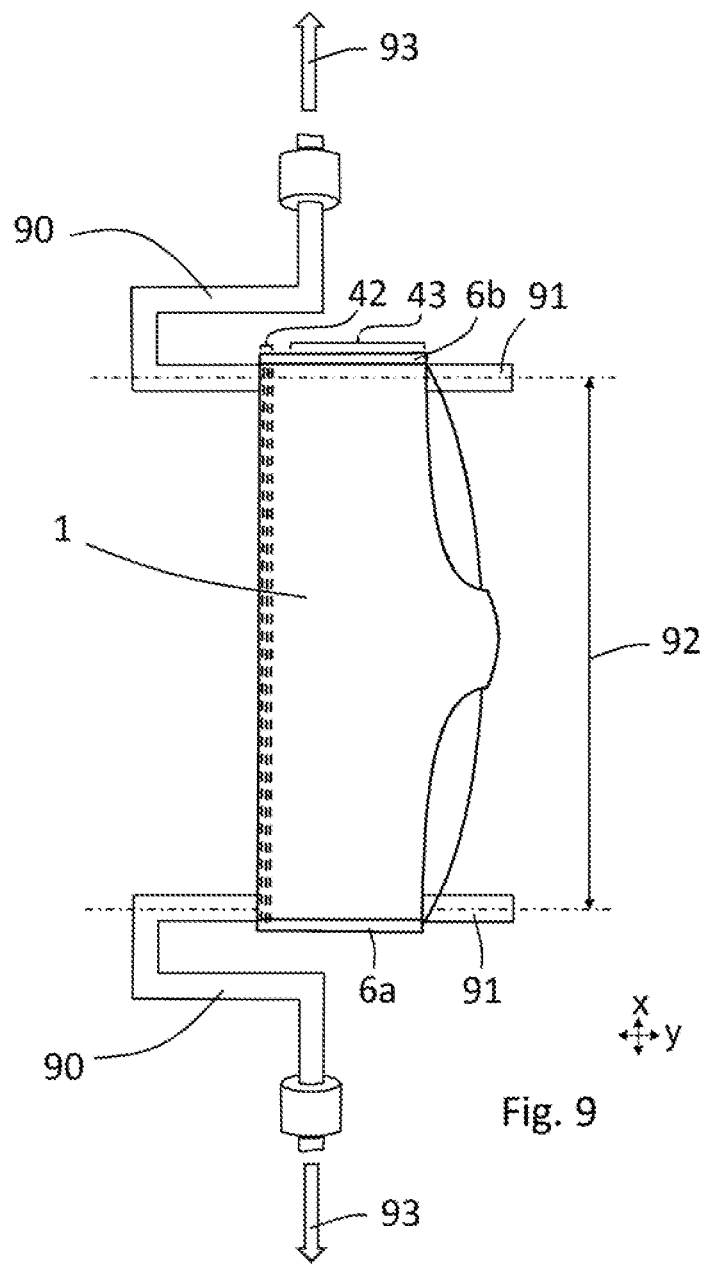
FIG. 9 shows the test equipment used for determining the circumferential length of the waist portion in an extended state and relaxed state of the absorbent article, as well as for determining the circumferential length of the body portion in the extended state of the absorbent article.

FIG. 9 schematically shows the test equipment used for measuring of the circumferential length of the waist portion 42 and body portion 43 in an extended state of the absorbent article 1, and for measuring the circumferential length of the waist portion 42 in a relaxed state of the absorbent article 1.

Measurements of the circumferential length of the waist portion 42 and body portion 43 in an extended state of the absorbent article 1 is performed by using any suitable tensile tester. The tensile tester that were used for obtaining the experimental data below was an Instron, model 4464, wherein the clamps 90 have been replaced with parallel upper and lower tube-formed cylinders 91 having a diameter of 60 millimetres and being oriented in the longitudinal direction Y of the absorbent article 1. The tube-formed cylinders are made of blank polished SS2333 stainless steel with smooth surface to provide low friction such that the absorbent articles do not stuck against the surface. The distance 92 between the cylinders 91 are initially set to correspond to the natural width of the absorbent article 1 such that the absorbent article can be mounted on the cylinders 91 in a natural state with the cylinders 91 placed inside the absorbent article 1 and with the cylinders 91 extending at least over the entire length of the side seams 6a, 6b. The cylinders 91 are subsequently pulled apart in the transverse direction X. The test is performed with a constant speed of 200 mm/minute up to 90 Newton tension force in which the tensile tester have been programmed to plot and/or sample data at least at 3 and 80 Newton.

For the measurements, new products were taken and unfolded and the test result is based on an average result of 5 tested products. The distance 92 between the centre of the cylinders 91 was measured when applying a specified force in opposite directions 93. The circumferential length of the waist portion 42 and body portion 43 in an extended state of the absorbent article 1 correspond to twice the distance 92 between the centre of the cylinders 91 plus the diameter 60 millimetres of the cylinders 91 multiplied with π, when the cylinders 91 have pulled apart the sides of the absorbent article 1 with a force of 80 Newton.

Measurements of the circumferential length of the waist portion 42 in a relaxed state of the absorbent article 1 is performed in the same test run, when the cylinders 91 have pulled apart the sides of the absorbent article 1 with a force of 3 Newton. The circumferential length of the waist portion Butylene-Styrene block copolymer co-extruded with polyolefin skin layers. The basis weight of the film is 35 gsm. The elastic film has been ultrasonically bonded to inner and outer spun bond nonwoven propylene layers having a basis weight of 16 gsm while the film was stretched to 240%.

The waist region of the female product comprises additional waist elastics in the form of 6 elastic threads of 940 dtex stretched to 230% elongation attached in the waist region between the film laminate and a cover strip of spunbond nonwoven.

The tested male product has the same construction, materials and same pitch length as the female product except for the additional added waist elastic. The waist region of the male product therefor only comprises the elastic film laminate.

Comparison between the products has been made at 3 N and at 80 N in accordance with the described test method. The resulting experimental data of ten tested absorbent articles, five male absorbent articles and five female absorbent articles, are showed below in Table 1 with measurement data. Table 1 includes, for each tested sample, the measured circumferential length in millimetres of the waist portion at various levels of tension in Newton. Table 1 also includes a row with averaged values of the five tested female and male articles, respectively.

TABLE 1

| Sample number | | Circumference (mm) | | | | | | | | | | |
|---|---|---|---|---|---|---|---|---|---|---|---|---|
| | | 1 N | 3 N | 5 N | 10 N | 15 N | 20 N | 30 N | 40 N | 45 N | 50 N | 55 N |
| 1 | Female | 457 | 570 | 654 | 732 | 792 | 852 | 972 | 1075 | 1118 | 1151 | 1178 |
| 2 | Female | 453 | 559 | 641 | 721 | 781 | 839 | 957 | 1061 | 1103 | 1139 | 1166 |
| 3 | Female | 451 | 557 | 648 | 730 | 789 | 847 | 964 | 1066 | 1108 | 1142 | 1170 |
| 4 | Female | 474 | 584 | 653 | 731 | 788 | 847 | 967 | 1071 | 1113 | 1148 | 1175 |
| 5 | Female | 479 | 584 | 660 | 738 | 795 | 854 | 973 | 1077 | 1119 | 1152 | 1178 |
| Average: | | 463 | 571 | 651 | 730 | 789 | 848 | 967 | 1070 | 1112 | 1146 | 1174 |
| 1 | Male | 636 | 693 | 729 | 803 | 880 | 957 | 1090 | 1172 | 1196 | 1216 | 1231 |
| 2 | Male | 634 | 692 | 727 | 796 | 868 | 943 | 1073 | 1159 | 1185 | 1205 | 1221 |
| 3 | Male | 639 | 690 | 724 | 799 | 873 | 950 | 1082 | 1164 | 1188 | 1207 | 1222 |
| 4 | Male | 638 | 691 | 725 | 796 | 869 | 945 | 1077 | 1159 | 1183 | 1203 | 1223 |
| 5 | Male | 637 | 693 | 730 | 804 | 880 | 957 | 1090 | 1172 | 1197 | 1216 | 1231 |
| Average: | | 637 | 692 | 727 | 799 | 874 | 950 | 1082 | 1165 | 1190 | 1209 | 1226 |

| Sample number | | Circumference (mm) | | | | | | | | | |
|---|---|---|---|---|---|---|---|---|---|---|---|
| | | 60 N | 65 N | 70 N | 75 N | 80 N | 85 N | 90 N | 80 N | 85 N | 90 N |
| 1 | Female | 1198 | 1215 | 1230 | 1243 | 1254 | 1262 | 1269 | 1254 | 1262 | 1269 |
| 2 | Female | 1187 | 1204 | 1219 | 1232 | 1242 | 1251 | 1258 | 1242 | 1251 | 1258 |
| 3 | Female | 1190 | 1206 | 1221 | 1233 | 1244 | 1252 | 1259 | 1244 | 1252 | 1259 |
| 4 | Female | 1196 | 1212 | 1227 | 1240 | 1250 | 1258 | 1265 | 1250 | 1258 | 1265 |
| 5 | Female | 1199 | 1215 | 1231 | 1243 | 1253 | 1262 | 1269 | 1253 | 1262 | 1269 |
| Average: | | 1194 | 1211 | 1226 | 1238 | 1249 | 1257 | 1264 | 1249 | 1257 | 1264 |
| 1 | Male | 1243 | 1253 | 1261 | 1268 | 1275 | 1282 | 1287 | 1275 | 1282 | 1287 |
| 2 | Male | 1234 | 1245 | 1254 | 1261 | 1268 | 1274 | 1281 | 1268 | 1274 | 1281 |
| 3 | Male | 1234 | 1244 | 1253 | 1261 | 1267 | 1274 | 1280 | 1267 | 1274 | 1280 |
| 4 | Male | 1236 | 1247 | 1256 | 1264 | 1271 | 1277 | 1283 | 1271 | 1277 | 1283 |
| 5 | Male | 1243 | 1252 | 1261 | 1268 | 1274 | 1281 | 1286 | 1274 | 1281 | 1286 |
| Average: | | 1238 | 1248 | 1257 | 1264 | 1271 | 1278 | 1283 | 1271 | 1278 | 1283 |

42 in the relaxed state of the absorbent article 1 correspond to twice the distance 92 between centre of the cylinders 91 plus the diameter 60 mm of the cylinders 91 multiplied with π, when the cylinders 91 have pulled apart the sides of the absorbent article 1 with a force of 3 N.

The tested female product is a product having back and front panels made of an elastic film laminate. The elastic film laminate comprises an elastic film of a Styrene-Ethylene/

Figure 10:
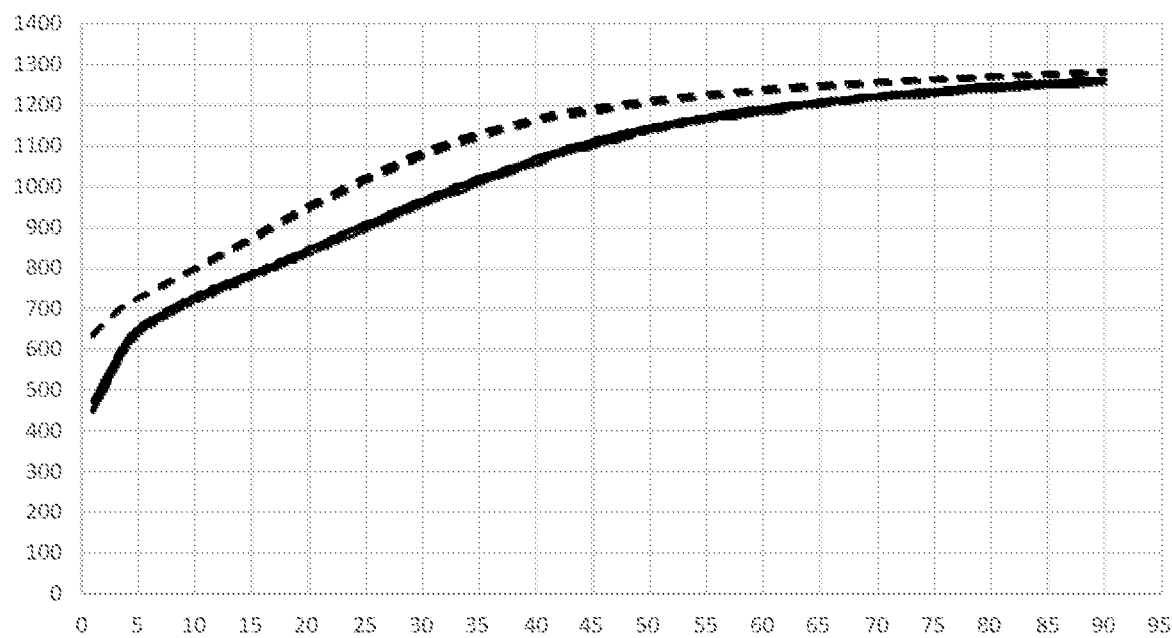
FIG. 10 illustrates Diagram 1 illustrating test data.

Furthermore, based on the data from Table 1 showed above, Diagram 1 included as FIG. 10, illustrates, for each of the ten tested absorbent articles, on the vertical axis measured circumferential length of the waist portion and on the horizontal axis the tension force applied by the cylinders of the testing equipment. The dotted lines correspond to the five tested male articles and the continuous lines correspond to the five tested female articles.

Figure 11:
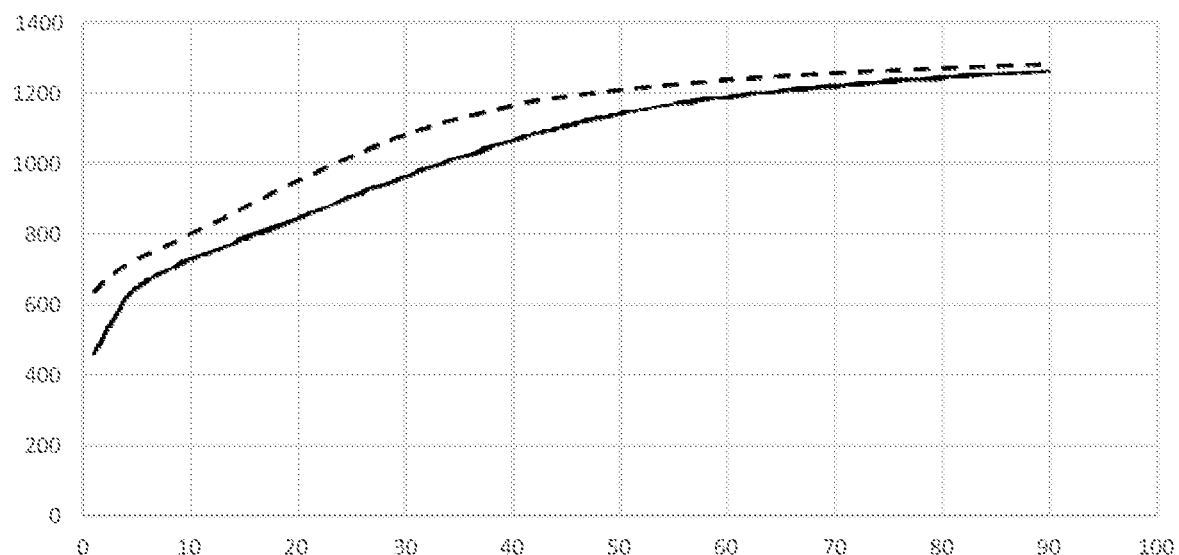
FIG. 11 illustrates Diagram 2 illustrating test data.

Furthermore, based on the data from Table 1, Diagram 2, included as FIG. 11, illustrates on the vertical axis an average measured circumferential length of the waist portion of the female and male absorbent articles, and on the horizontal axis the tension force applied by the cylinders of the testing equipment. The dotted line correspond to the average value of the five tested male articles and the continuous lines correspond to the average value of the five tested female articles The experimental data shows that, in a relaxed state, i.e. at 3 Newton tension force, the average difference in width of the elasticised waist portion 42 of the male and female absorbent articles is about 21%, and that in an extended state, i.e. at 80 Newton tension force, the average difference in width of the elasticised waist portion 42 of the male and female absorbent articles is only about 2%.

This experimental data thus confirms that underlying concept of the present disclosure that at least one female absorbent article and at least one male absorbent article of the array of disposable pant-type gender-specific absorbent articles shares essentially the same geometry and dimension of the front and back panels 3, 4 in an extended state, such that the cost for an array of gender-specific absorbent articles is kept relatively low, while the shape and form of the male and female absorbent articles in a relaxed state of the array is adapted to have a better fit for each specific gender, wherein the shape and form of the male and female absorbent articles in a relaxed and extended state of the array is adapted by varying the degree of gathering of the sheet material of the front and/or back panel in the transverse direction X. Moreover, the circumferential length of the waist portion in a relaxed state can be varied and adapted relatively cost-efficiently by for example adapting the waist and/or body elastic feature.

The experimental data included above is merely one example of an average difference in width of the elasticised waist portion 42 of the male and female absorbent articles at 3 and 80 Newton, and other levels of average difference in width of the elasticised waist portion 42 of the male and female absorbent articles at 3 and 80 Newton can be different while still solving the problem of providing improved absorbent articles in terms of comfort, fit and discrete underwear-like visual appearance while maintaining a low manufacturing cost is desirable. For example, the objective problem is solved also when the difference in width, at 3 Newton tension force, is at least 10%, and specifically more than 15%, while the difference in width, at 80 Newton tension force, is less than 5%, and specifically less than 3%.

By "absorbent article" is meant an article that absorbs or is adapted to absorb bodily fluids, such as urine and/or blood.

The nonwoven material layers or webs of the present disclosure forming the front and back panels may for example be selected from, for example, of spunbond, air laid, wet laid, carded, electro spunned or meltblown nonwovens. The nonwoven material may be bonded by multiple techniques, e.g. by needling, hydroentangling, or heat bonding.

The nonwoven material of the disclosed absorbent articles is a mixture of natural and synthetic materials. Natural fibres are for instance cellulosic fibres or fibres from regenerated cellulose.

The term "elastic thread" is intended to mean an elastic strand or elastic thread which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The threads may be of the elastane type that is available under the trade name "LYCRA", but any suitable elastic thread may be used. The threads may have a linear mass density, dtex, of about 80-1200 dtex.

In certain embodiments, the elastic threads are elongated during the production process from about 50 to about 300% of the initial, non-tensioned original length, more preferably 100-250% and most preferably 150-220% of the initial, non-tensioned original length. The elastic threads should preferably be of a type that are able to tolerate an elongation of at least about 200% without breaking, so that they can be safely used in the production process without risk for breaking.

Further information with respect to material about the elastic web material is disclosed in WO2014098683 A1, which is incorporated by reference herein in its entirety for all purposes.

The absorbent core 5 may comprise any conventional material suitable for absorbing discharged bodily wastes, such as cellulosic fluff pulp, tissue layers, highly absorbent polymers (super absorbents), absorbent foam materials including hydrogel-foam material, absorbent nonwoven materials or the like.

The absorbent core 5 may have a liquid permeable topsheet placed on the side intended to face the skin of a user, and a liquid impermeable backsheet placed on the side of the absorbent body intended to face the garment of a user. Generally, the liquid permeable topsheet comprises or consist of a nonwoven material. The topsheet material may further be composed of tow fibres, porous foams, apertured plastic films etc. As mentioned above, the materials suited as topsheet materials should be soft and non-irritating to the skin and be readily penetrated by body fluid, e.g. urine or menstrual fluid, and display low rewetting properties.

The liquid impermeable backsheet may consist of or comprise a thin plastic film, e.g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent body, while still preventing liquids from passing through the backsheet material.

The topsheet and backsheet may be connected to each other for example by adhesive bonding, gluing or welding by heat or ultrasonic. The topsheet and/or the backsheet may further be attached to the absorbent body by any method known in the art, such as adhesive, heat-bonding etc.

The topsheet and backsheet of the absorbent core 5 may extend outwardly beyond the area of the absorbent core 5, thereby defining an absorbent insert 2 comprising an absorbent core 5. The maximal width of the absorbent core 5 is typically about 80 to 150 mm in transverse direction X, and the maximal length L6 of the absorbent core 5 is typically and 400 to 600 mm in longitudinal direction Y.

The absorbent core 5 may overlap the front panel 3 with a length of about 50-100 mm. Moreover, the absorbent core 5 may overlap the body panel 4 with a length of about 200-250 mm; alternatively, the absorbent core 5 may overlap the main section 28 of the back panel 4 with a length of about 30-70 mm.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

The invention claimed is:

1. An array of disposable pant-type gender-specific absorbent articles adapted for female and male users, the array comprises:
   a first subarray of absorbent articles including a first size absorbent article adapted for female users and a second size absorbent article adapted for female users,
   a second subarray of absorbent articles including a third size absorbent article for male users and a fourth size absorbent article adapted for male users,
   wherein each absorbent article of the array has a longitudinal direction (Y) and a transverse direction (X) and comprises:
   a front panel having a waist edge and a pair of side edges,
   a back panel having a waist edge and a pair of side edges,
   an absorbent insert located mainly in a crotch portion of the absorbent article and being connected to the front and back panels and having an absorbent core,
   wherein the front and back panels are joined to each other at opposite side edges by side seams forming a waist opening and two leg openings,
   wherein each absorbent article in the array comprises a transversely elasticised waist portion extending along the waist opening and a transversely elasticised body portion located adjacent to the waist portion,
   wherein at least one of said first and second size absorbent articles has a first circumferential length of the waist portion in a relaxed state and a second circumferential length of the waist portion in an extended state, and at least one of said third and fourth size absorbent articles has a third circumferential length of the waist portion in a relaxed state and a fourth circumferential length of the waist portion in an extended state,
   wherein the circumferential length of the waist portion in the relaxed state is measured according to the method described in the specification with a tension of 3 Newton, and the circumferential length of the waist portion in the extended state is measured according to the method described in the specification with a tension of 80 Newton,
   wherein the third circumferential length is more than 10% larger than the first circumferential length, and the fourth circumferential length is less than 5% larger than the second circumferential length,
   wherein one of the front panel or the rear panel of each of the absorbent articles in the first subarray has a first change of width from the relaxed state to the extended state in the transverse direction, and the corresponding panel of each of the absorbent articles in the second subarray has a second change of width from the relaxed state to the extended state in the transverse direction, wherein the first change of width is greater than the second change of width.

2. An array according to claim 1, wherein the circumferential length of the waist portion in the extended state of the first size absorbent article is smaller than the circumferential length of the waist portion in the extended state of the second size absorbent article.

3. An array according to claim 1, wherein the circumferential length of the waist portion in the extended state of the third size absorbent article is smaller than the circumferential length of the waist portion in the extended state of the fourth size absorbent article.

4. An array according to claim 1, wherein the circumferential length of the waist portion in the extended state of the first size absorbent article is substantially equal with the circumferential length of the waist portion in the extended state of the third size absorbent article.

5. An array according to claim 1, wherein the circumferential length of the waist portion in the extended state of the second size absorbent article is substantially equal with the circumferential length of the waist portion in the extended state of the fourth size absorbent article.

6. An array according to claim 1, wherein the circumferential length of the waist portion in the relaxed state of the first size absorbent article is smaller than the circumferential length of the waist portion in the relaxed state of the third size absorbent.

7. An array according to claim 1, wherein the circumferential length of the waist portion in the relaxed state of the second size absorbent article is smaller than the circumferential length of the waist portion in the relaxed state of the fourth size absorbent article.

8. An array according to claim 1, wherein a circumferential length of the body portion in an extended state is measured according to the method described in the specification with a tension of 80 Newton, and wherein the circumferential length of the body portion in the extended state of the first size absorbent article is smaller than the circumferential length of the body portion in the extended state of the second size absorbent article.

9. An array according to claim 1, wherein a circumferential length of the body portion in an extended state is measured according to the method described in the specification with a tension of 80 Newton, and wherein the circumferential length of the body portion in the extended state of the third size absorbent article is smaller than the circumferential length of the body portion in the extended state of the fourth size absorbent article.

10. An array according to claim 1, wherein a circumferential length of the body portion in an extended state is measured according to the method described in the specification with a tension of 80 Newton, and wherein the circumferential length of the body portion in the extended state of the first size absorbent article is substantially equal with the circumferential length of the body portion in the extended state of the third size absorbent article.

11. An array according to claim 1, wherein a circumferential length of the body portion in an extended state is measured according to the method described in the specification with a tension of 80 Newton, and wherein the circumferential length of the body portion in the extended state of the second size absorbent article is substantially equal with the circumferential length of the body portion in the extended state of the fourth size absorbent article.

12. An array according to claim 1, wherein each absorbent article in the array comprises a first acute angle defined by a first line extending between an uppermost point of the side seam and a lowermost point of the side seam with the absorbent article in a relaxed state and a second line extending in the longitudinal direction (Y), and wherein the first acute angle of each of the first and second size absorbent articles is larger than the first acute angle of each of the third and fourth size absorbent articles.

13. The array according to claim 1, wherein a smallest longitudinal distance between a side edge of the front panel and an oppositely located side edge of the back panel of each absorbent article in the array is essentially the same.

14. An array according to claim 1, wherein each front panel in the array comprises a first elastic region and a second elastic region, and wherein each back panel in the array comprises a third elastic region and a fourth elastic region, wherein the first and third elastic regions define the transversely elasticised waist portion extending along the waist opening and the second and fourth elastic regions define the transversely elasticised body portion.

15. An array according to claim 1, wherein the transversely elasticised waist portion and/or the transversely elasticised body portion comprises an elastic web material, such as an elastic nonwoven or elastic film laminate.

16. The array according to claim 1, wherein the front and back panels of each absorbent article in the array are made of individual parts that are mutually interconnected by means of the absorbent insert, or wherein the front and back panels are integral parts of a single-piece chassis made of one piece of web material having cut-out leg openings, wherein the absorbent body is located overlapping a crotch portion of the chassis.

17. The array according to claim 1, wherein the absorbent articles in the array are pant diapers or sanitary pants or incontinence pants.

18. An array of packages comprising the array of disposable pant-type gender-specific absorbent articles according to claim 1, wherein the first subarray of absorbent articles includes a plurality of first size absorbent articles adapted for female users and packed in a first package, and a plurality of second size absorbent articles adapted for female users and packed in a second package, wherein the second subarray of absorbent articles includes a plurality of third size absorbent articles for male users and packed in a third package, and a plurality of fourth size absorbent articles adapted for male users and packed in a fourth package, wherein each of the first to fourth packages in the array of packages comprises an external marking indicating the size and/or suitable gender of the disposable pant-type absorbent articles therein.

19. An array according to claim 1, wherein the circumferential length of the waist portion in the extended state of the first size absorbent article is substantially equal with the circumferential length of the waist portion in the extended state of the third size absorbent article.

20. An array according to claim 19, wherein the circumferential length of the waist portion in the extended state of the second size absorbent article is substantially equal with the circumferential length of the waist portion in the extended state of the fourth size absorbent article.

21. An array according to claim 1, wherein the third circumferential length is more than 15% larger than the first circumferential length.

22. An array according to claim 1, wherein the fourth circumferential length is less than 3% larger than the second circumferential length.

23. An array according to claim 1, wherein the circumferential length of the waist portion in the extended state of at least one of the first size absorbent article and the second size absorbent article is essentially the same as the circumferential length of the waist portion in the extended state of at least one of the third size absorbent article and the fourth size absorbent article.

24. An array according to claim 23, wherein the circumferential length of the waist portion in the relaxed state of the at least one of the first size absorbent article and the second size absorbent article is smaller than the circumferential length of the waist portion in the relaxed state of the at least one of the third size absorbent article and the fourth size absorbent article.

25. An array of disposable pant-type gender-specific absorbent articles adapted for female and male users, the array comprises:
- a first subarray of absorbent articles including a first size absorbent article adapted for female users and a second size absorbent article adapted for female users,
- a second subarray of absorbent articles including a third size absorbent article for male users and a fourth size absorbent article adapted for male users,
- wherein each absorbent article of the array has a longitudinal direction (Y) and a transverse direction (X) and comprises:
- a front panel having a waist edge and a pair of side edges,
- a back panel having a waist edge and a pair of side edges,
- an absorbent insert located mainly in a crotch portion of the absorbent article and being connected to the front and back panels and having an absorbent core,
- wherein the front and back panels are joined to each other at opposite side edges by side seams forming a waist opening and two leg openings,
- wherein each absorbent article in the array comprises a transversely elasticised waist portion extending along the waist opening and a transversely elasticised body portion located adjacent to the waist portion,
- wherein at least one of said first and second size absorbent articles has a first circumferential length of the waist portion in a relaxed state and a second circumferential length of the waist portion in an extended state, and at least one of said third and fourth size absorbent articles has a third circumferential length of the waist portion in a relaxed state and a fourth circumferential length of the waist portion in an extended state,
- wherein the circumferential length of the waist portion in the relaxed state is measured according to the method described in the specification with a tension of 3 Newton, and the circumferential length of the waist portion in the extended state is measured according to the method described in the specification with a tension of 80 Newton,
- wherein the third circumferential length is more than 10% larger than the first circumferential length, and the fourth circumferential length is less than 5% larger than the second circumferential length, and
- wherein each absorbent article in the array comprises a second acute angle defined by a third line running through the lowermost point of the side seam and a point along the front leg edge at a distance of 5 cm from the lowermost point of the side seam in the transverse direction (X) with the article in a relaxed state and a fourth line running in the transverse direction (X), and wherein the second acute angle of each of the first and second size absorbent articles is larger than the second acute angle of each of the third and fourth size absorbent articles.

26. An array of disposable pant-type gender-specific absorbent articles adapted for female and male users, the array comprises:
- a first subarray of absorbent articles including a first size absorbent article adapted for female users and a second size absorbent article adapted for female users, a second subarray of absorbent articles including a third size absorbent article for male users and a fourth size absorbent article adapted for male users, wherein each absorbent article of the array has a longitudinal direction (Y) and a transverse direction (X) and comprises:

a front panel having a waist edge and a pair of side edges, a back panel having a waist edge and a pair of side edges, an absorbent insert located mainly in a crotch portion of the absorbent article and being connected to the front and back panels and having an absorbent core wherein the front and back panels are joined to each other at opposite side edges by side seams forming a waist opening and two leg openings, wherein each absorbent article in the array comprises a first acute angle defined by a first line extending between an uppermost point of the side seam and a lowermost point of the side seam with the absorbent article in a relaxed state and a second line extending in the longitudinal direction (Y), and wherein the first acute angle of each of the first and second size absorbent articles is larger than the first acute angle of each of the third and fourth size absorbent articles, wherein one of the front panel or the rear panel of each of the absorbent articles in the first subarray has a first change of width from the relaxed state to the extended state in the transverse direction, and the corresponding panel of each of the absorbent articles in the second subarray has a second change of width from the relaxed state to the extended state in the transverse direction, wherein the first change of width is greater than the second change of width.

27. An array according to claim 26, wherein each absorbent article in the array comprises a second acute angle defined by a third line running through the lowermost point of the side seam and a point along the front leg edge at a distance of 5 cm from the lowermost point of the side seam in the transverse direction (X) with the article in a relaxed state and a fourth line running in the transverse direction (X), and wherein the second acute angle of each of the first and second size absorbent articles is larger than the second acute angle of each of the third and fourth size absorbent articles.

* * * * *